US012376864B2

(12) United States Patent
Kaneda et al.

(10) Patent No.: US 12,376,864 B2
(45) Date of Patent: Aug. 5, 2025

(54) MEDICAL INSTRUMENT SUITABLE FOR LIGATURE OR SIMILAR

(71) Applicants: JICHI MEDICAL UNIVERSITY, Tokyo (JP); TEIJIN MEDICAL TECHNOLOGIES CO., LTD., Osaka (JP)

(72) Inventors: Yuji Kaneda, Tochigi (JP); Yasuhiro Kawabe, Osaka (JP); Katsuhiro Mikami, Osaka (JP); Masumi Hirata, Osaka (JP)

(73) Assignees: JICHI MEDICAL UNIVERSITY, Tochigi (JP); TEIJIN MEDICAL TECHNOLOGIES CO., LTD., Osaka (JP)

( * ) Notice: Subject to any disclaimer, the term of this patent is extended or adjusted under 35 U.S.C. 154(b) by 300 days.

(21) Appl. No.: 17/914,504

(22) PCT Filed: Mar. 19, 2021

(86) PCT No.: PCT/JP2021/011478
§ 371 (c)(1),
(2) Date: Sep. 26, 2022

(87) PCT Pub. No.: WO2021/193463
PCT Pub. Date: Sep. 30, 2021

(65) Prior Publication Data
US 2023/0129423 A1    Apr. 27, 2023

(30) Foreign Application Priority Data
Mar. 24, 2020    (JP) ................................. 2020-053425

(51) Int. Cl.
*A61B 17/122*    (2006.01)
*A61B 17/00*    (2006.01)

(52) U.S. Cl.
CPC .. *A61B 17/122* (2013.01); *A61B 2017/00004* (2013.01)

(58) Field of Classification Search
CPC ......... Y10T 24/44932; Y10T 24/44752; A61B 17/122; A61B 2017/00004; A61B 17/12;
(Continued)

(56) References Cited

U.S. PATENT DOCUMENTS 3,705,586 A   12/1972  Sarracino
4,390,019 A    6/1983  Leveen
(Continued)

FOREIGN PATENT DOCUMENTS

CN      207755326 U    8/2018
JP      S 56-500242 A  3/1981
(Continued)

OTHER PUBLICATIONS

Supplementary European Search Report—EP 21 77 4532 dated Mar. 15, 2024, 2 pgs.
PCT ISR dated Jun. 8, 2021 w/English translation (5pgs).

*Primary Examiner* — Katherine M Shi
(74) *Attorney, Agent, or Firm* — Lippes Mathias LLP

(57) ABSTRACT

A medical instrument, comprising a flexible band body having a distal end and a proximal end; a flexible first rod-shaped body having a distal end and a proximal end; and a flexible second rod-shaped body having a distal end and a proximal end, wherein the distal end of the band body and the proximal end of the first rod-shaped body are connected, the distal end of the first rod-shaped body and the proximal end of the second rod-shaped body are connected via a connecting portion, the band body is more flexible than the first rod-shaped body and the second rod-shaped body, the second rod-shaped body has a locking part, the band body has a locking corresponding part, when tightened the locking part and the locking corresponding part, the proximal (Continued)

end of the first rod-shaped body and the distal end of the second rod-shaped body are connected via a part of the band body, the connecting portion is inflected, and a loop having a desired size can be formed by the first rod-shaped body, the second rod-shaped body and the part of the band body, and the second rod-shaped body further has a feature for placing the rest of the band body along an outer surface of the second rod-shaped body in the direction from the distal end to the proximal end of the second rod-shaped body when had been tightened the locking part and the locking corresponding part.

17 Claims, 24 Drawing Sheets

(58) Field of Classification Search
CPC ........ A61B 2017/12004; A61B 17/132; A61B 17/1322; A61B 17/1327; A61B 2017/00862; A61B 17/08; A61B 2017/081; A61B 17/083; A61B 2017/12018

See application file for complete search history.

(56) References Cited

U.S. PATENT DOCUMENTS

| | | | |
|---|---|---|---|
| 11,337,704 B2 | 5/2022 | Kaneda | |
| 2012/0083803 A1* | 4/2012 | Patel | A61B 17/1285 606/157 |
| 2016/0324527 A1 | 11/2016 | Thompson et al. | |
| 2018/0036008 A1 | 2/2018 | Ramsey et al. | |
| 2019/0133590 A1 | 5/2019 | Richard | |
| 2020/0046359 A1 | 2/2020 | Thomas et al. | |
| 2021/0161534 A1* | 6/2021 | Kaneda | A61B 17/12009 |

FOREIGN PATENT DOCUMENTS

| | | |
|---|---|---|
| JP | H 1-145536 A | 6/1989 |
| JP | H 5-337123 A | 12/1993 |
| JP | H 8-215201 A | 8/1996 |
| JP | 2002-508986 A | 3/2002 |
| JP | 2004-298501 A | 10/2004 |
| JP | 2006-87671 A | 4/2006 |
| JP | 2015-523144 A | 8/2015 |
| JP | 2016-165427 A | 9/2016 |
| JP | 2020-25856 A | 2/2020 |
| WO | WO 2019/039586 A1 | 2/2019 |

* cited by examiner

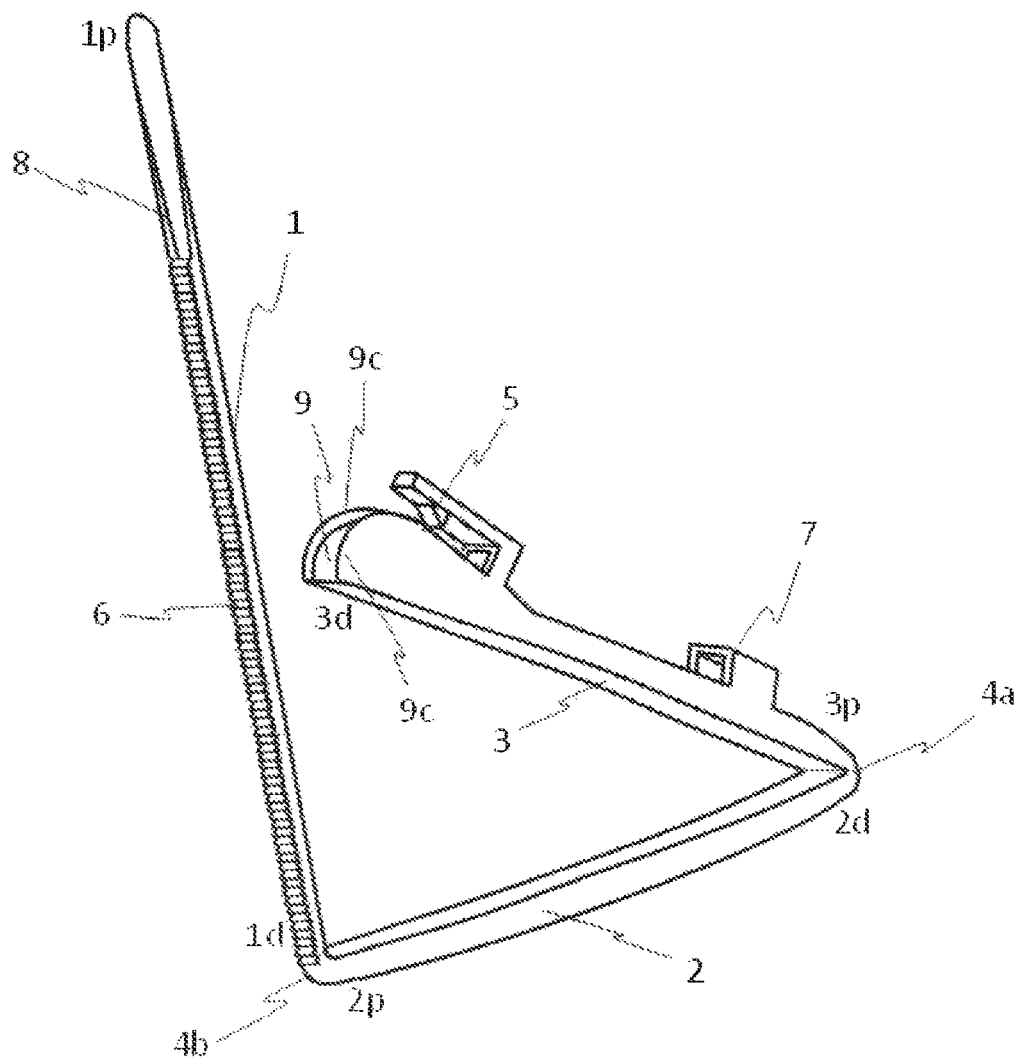
[FIG. 1]

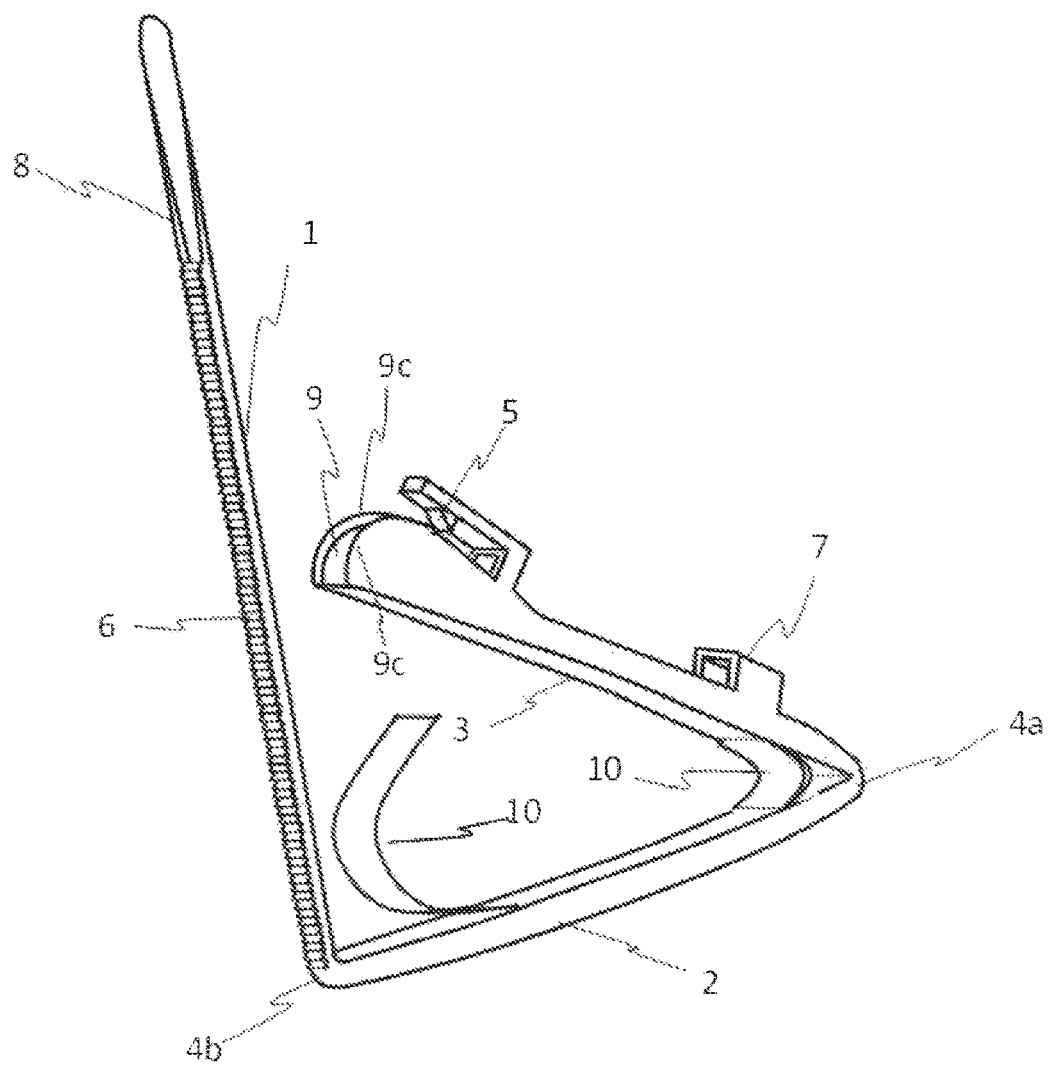
[FIG. 2]

[FIG. 3]
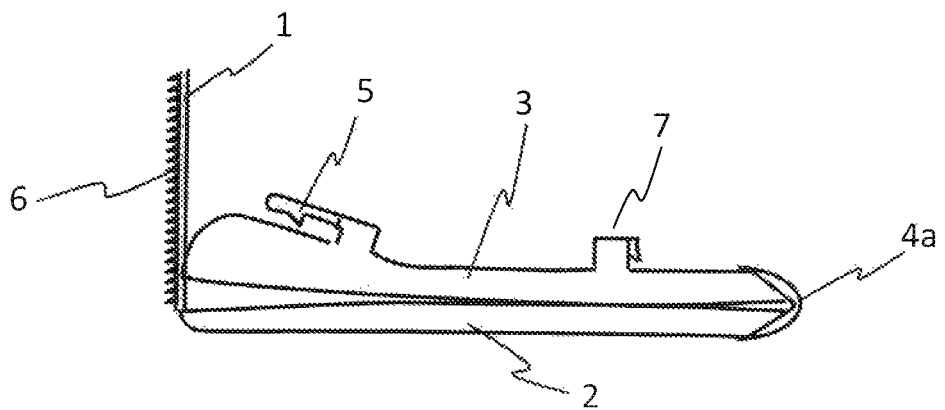
[FIG. 4]
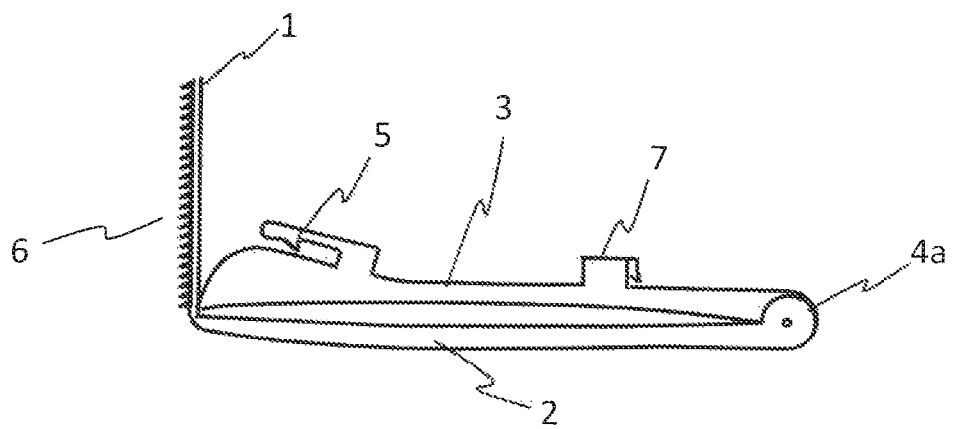

[FIG. 5]
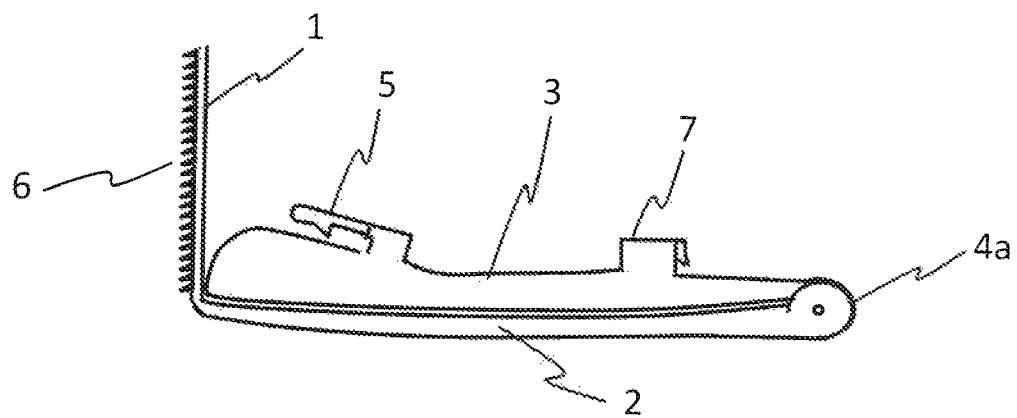
[FIG. 6]
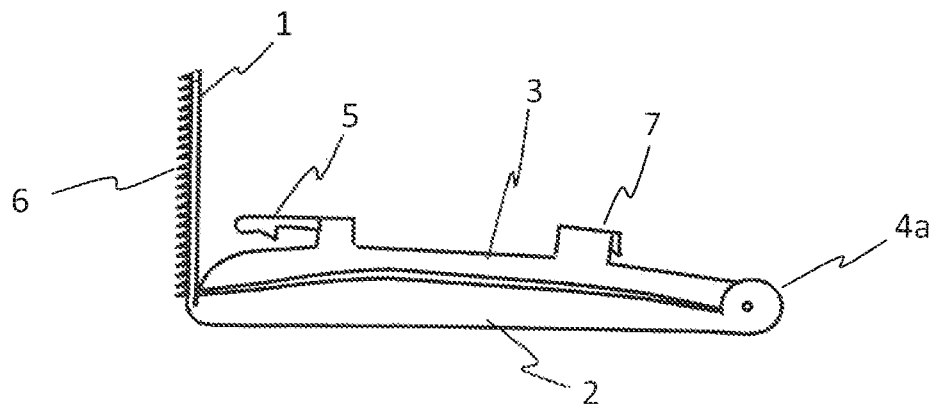

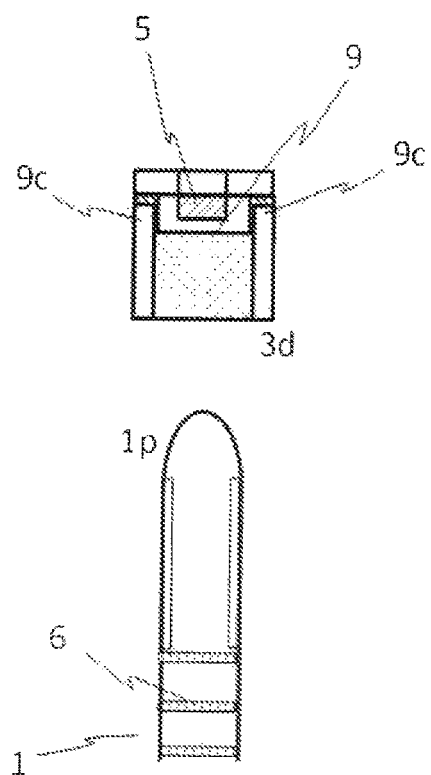
[FIG. 7]

[FIG. 8]
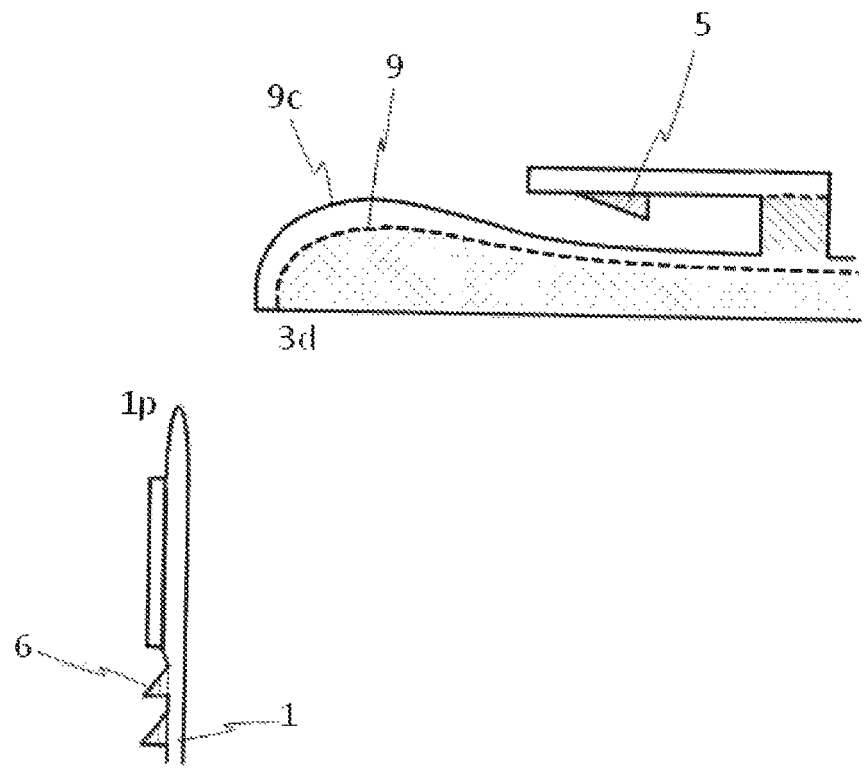
[FIG. 9]
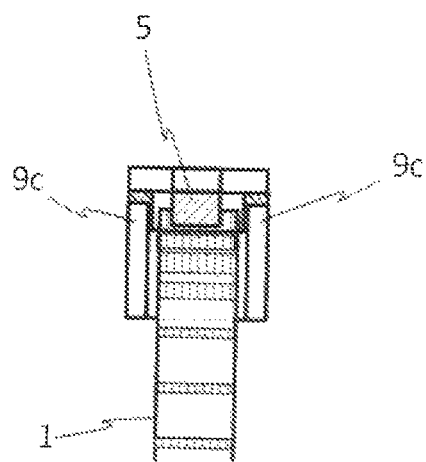

[FIG. 10]
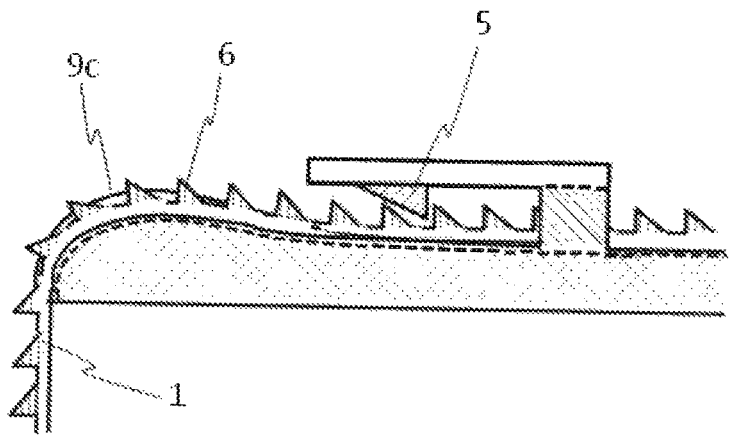
[FIG. 11]
3
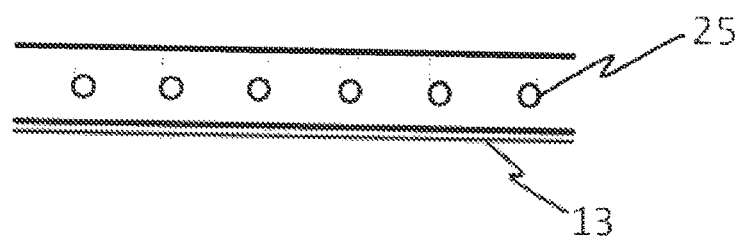
[FIG. 12]
3
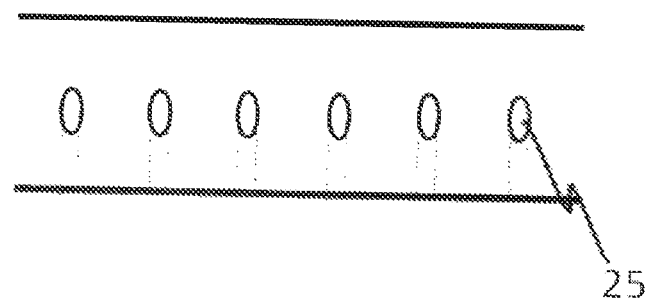

[FIG. 13]
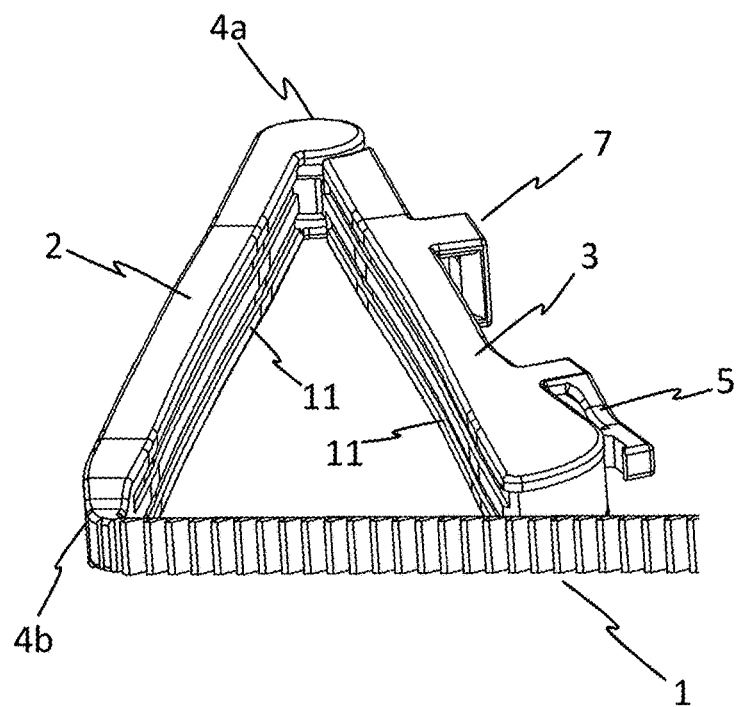
[FIG. 14]
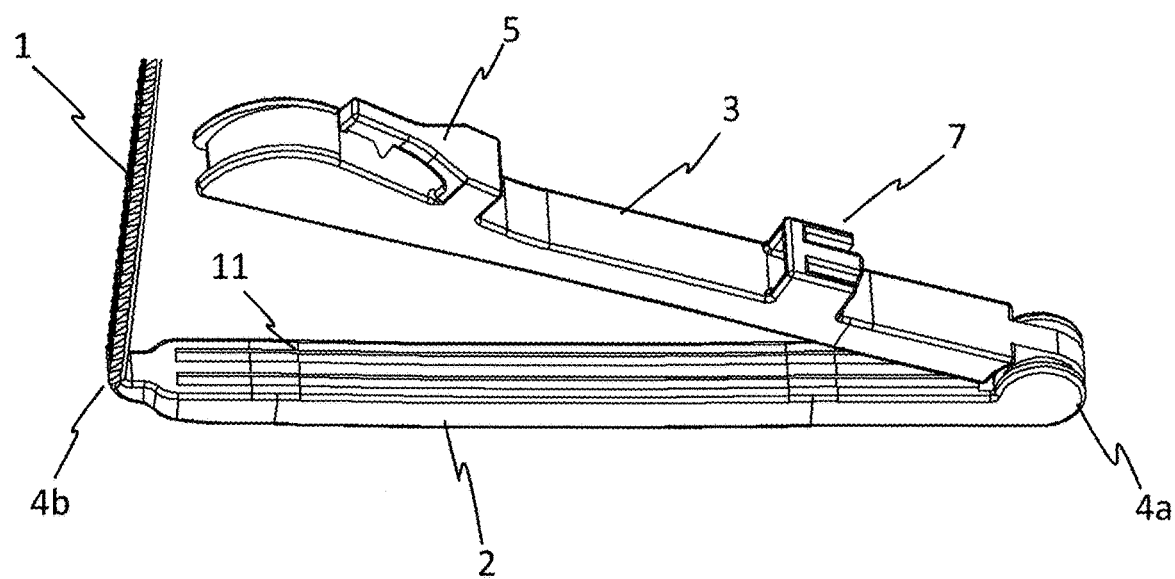

[FIG. 15]
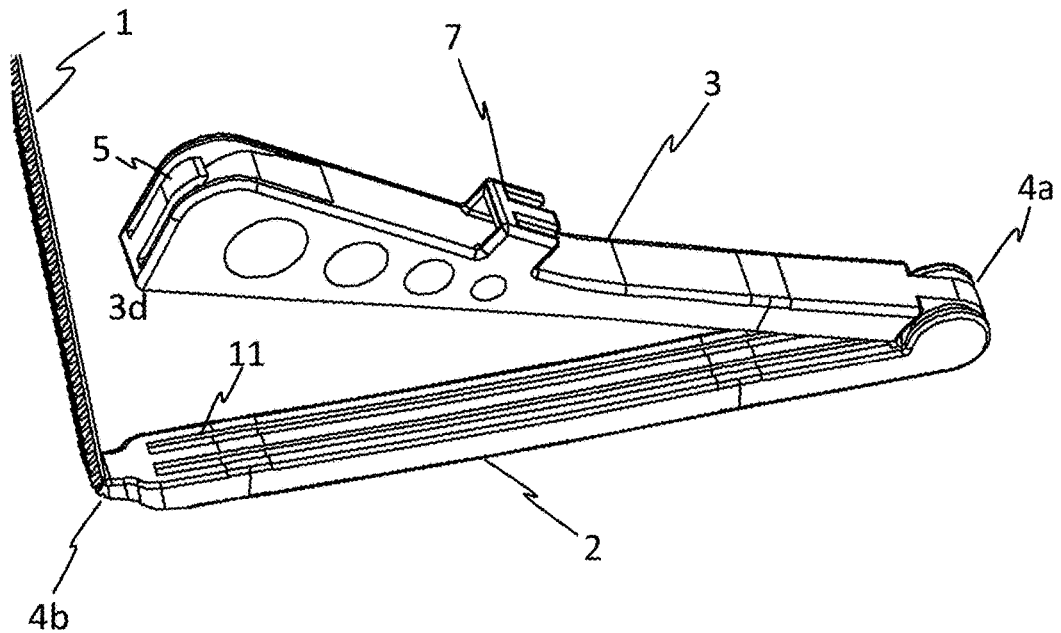
[FIG. 16]
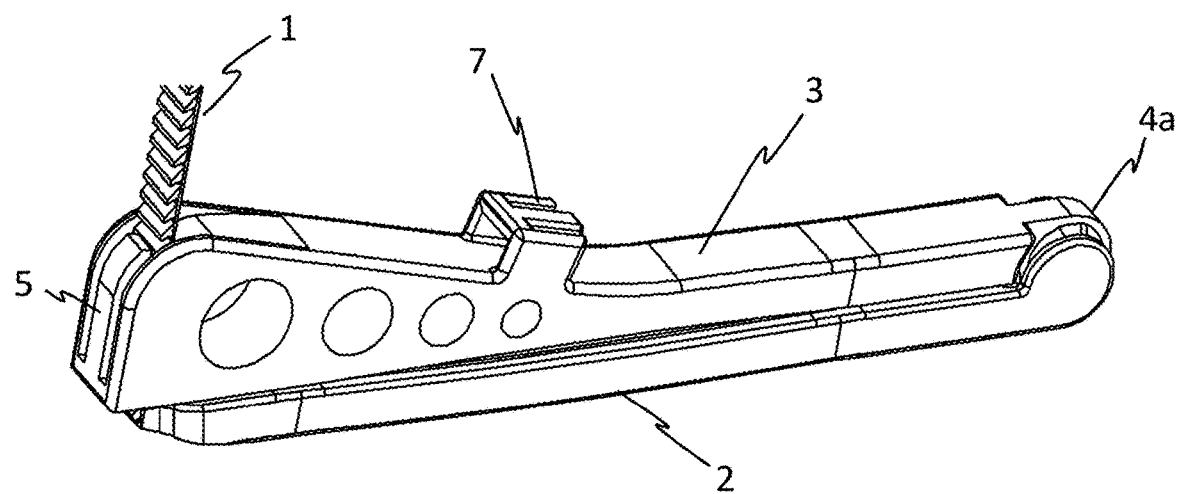

[FIG. 17]
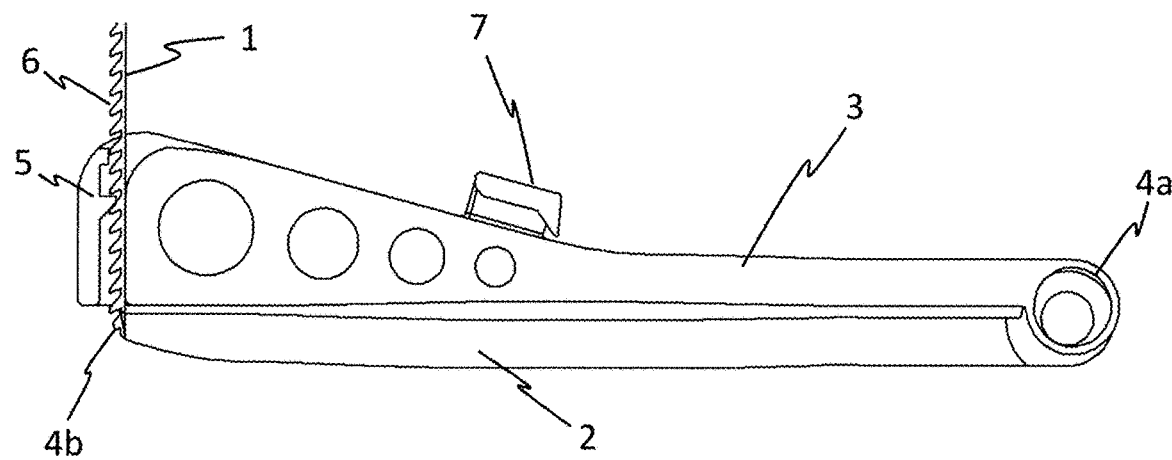
[FIG. 18]
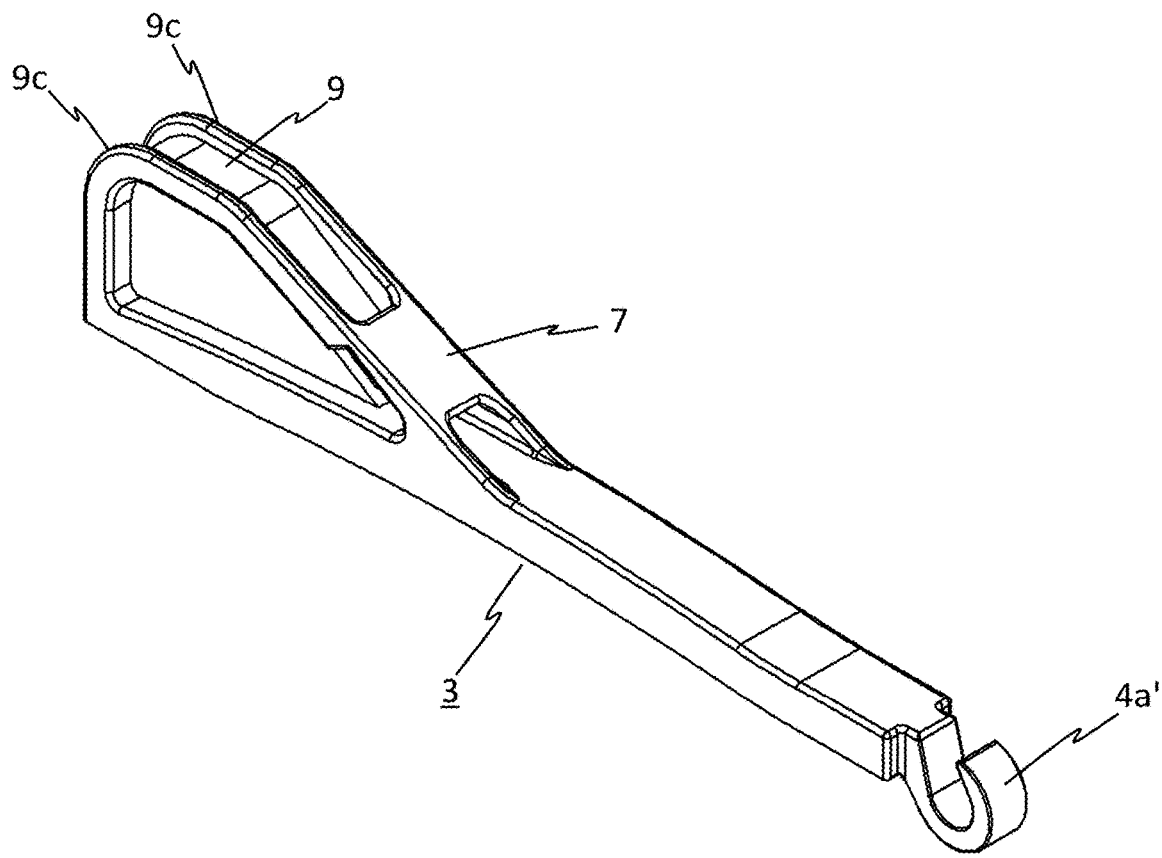

[FIG. 19]
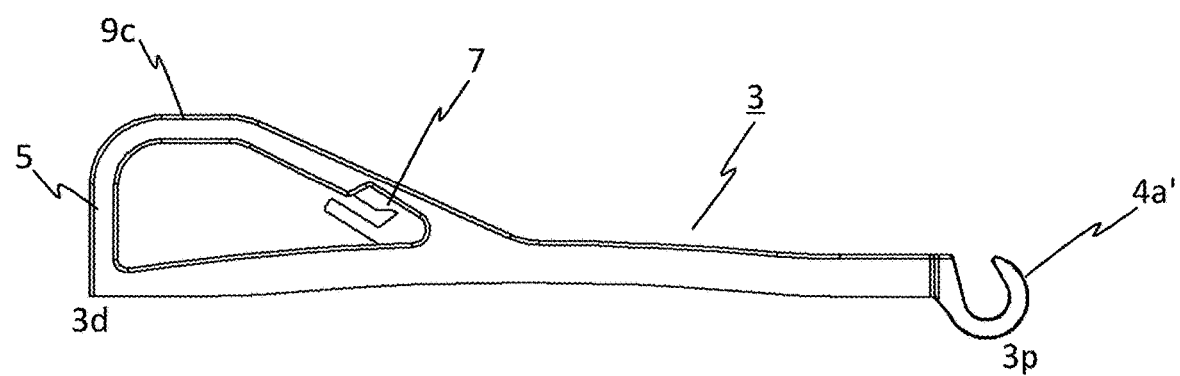

[FIG. 20]
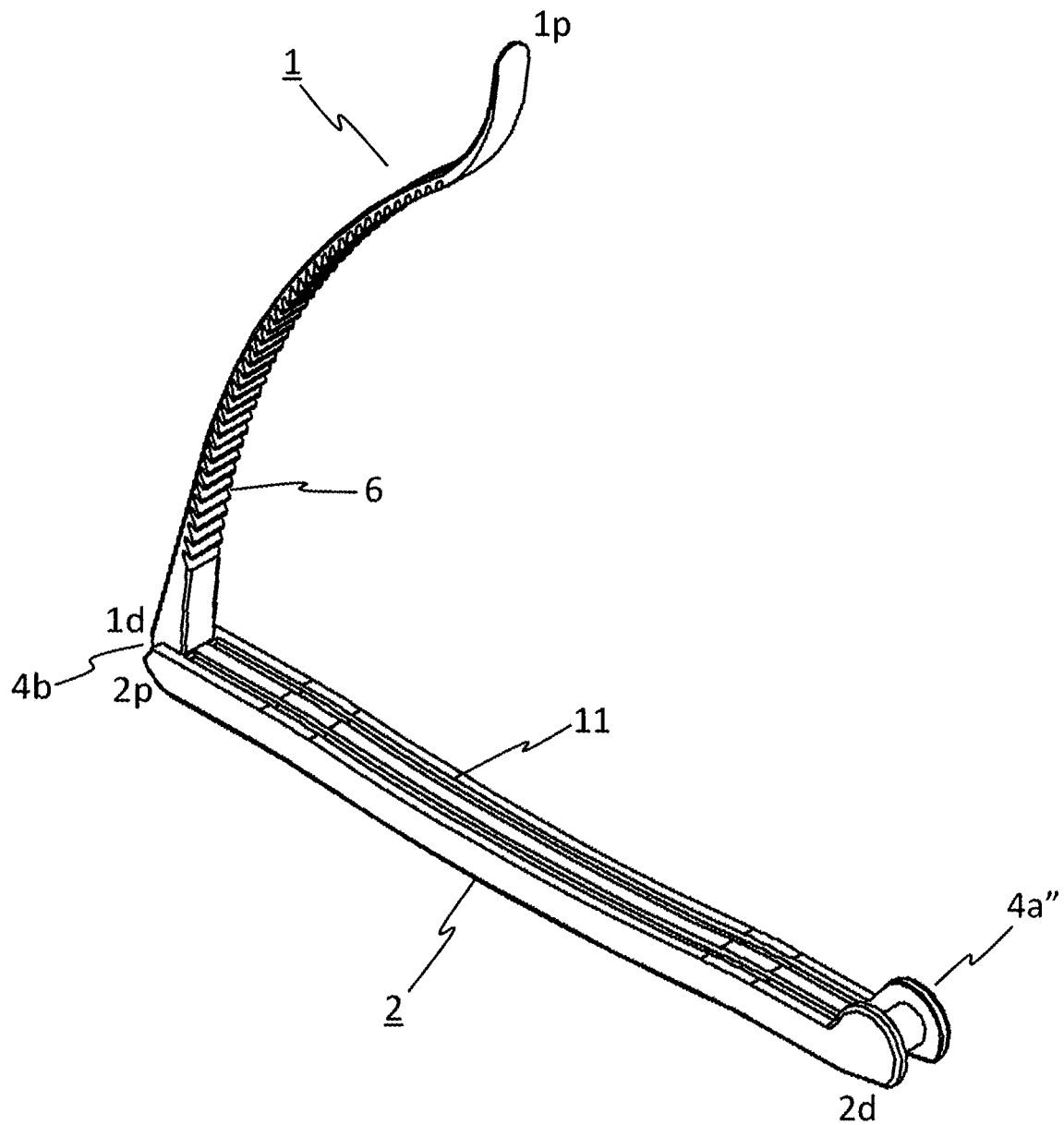

[FIG. 21]
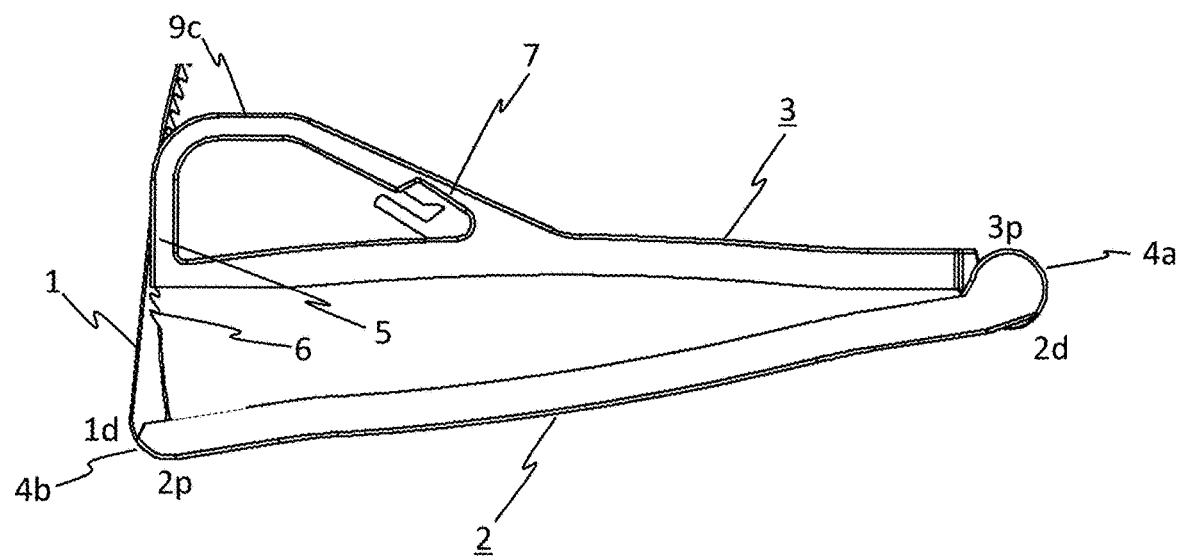
[FIG. 22]
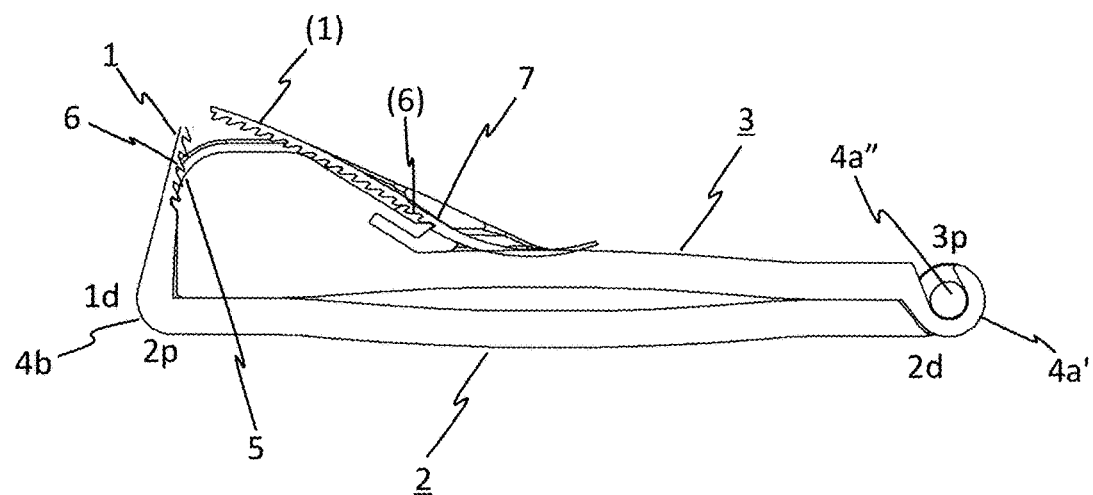

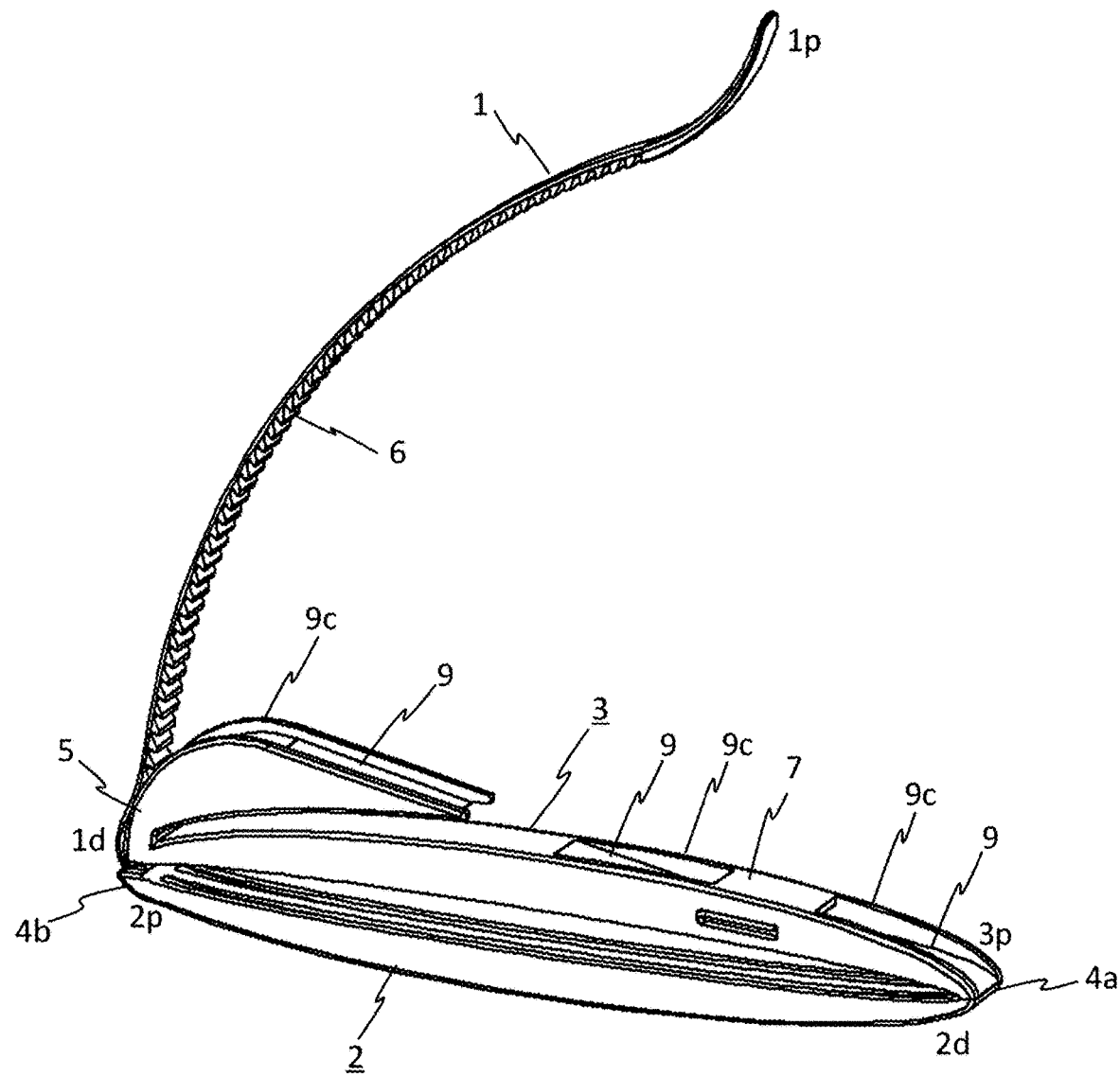
[FIG. 23]

[FIG. 24]
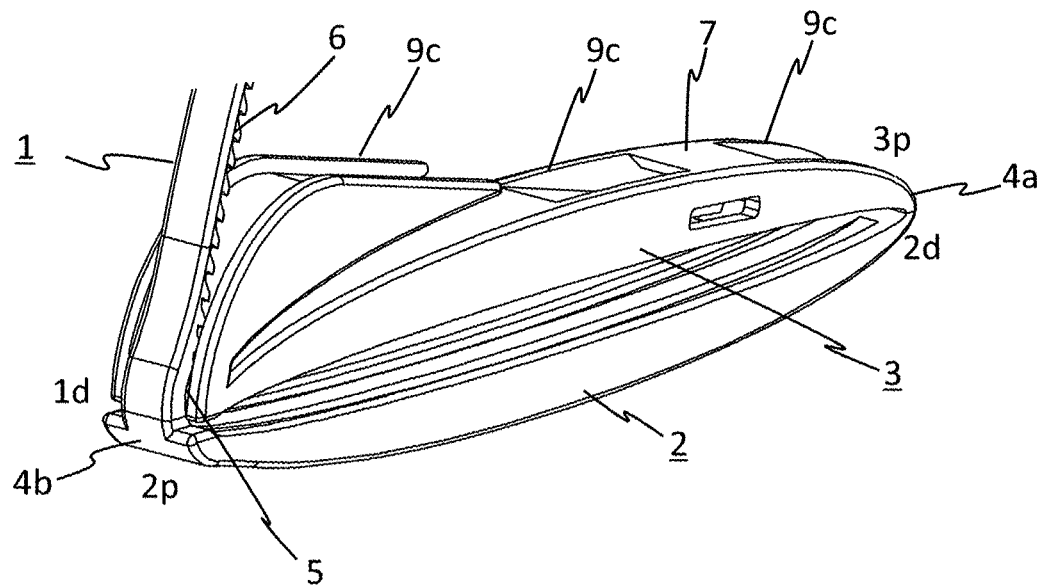
[FIG. 25]
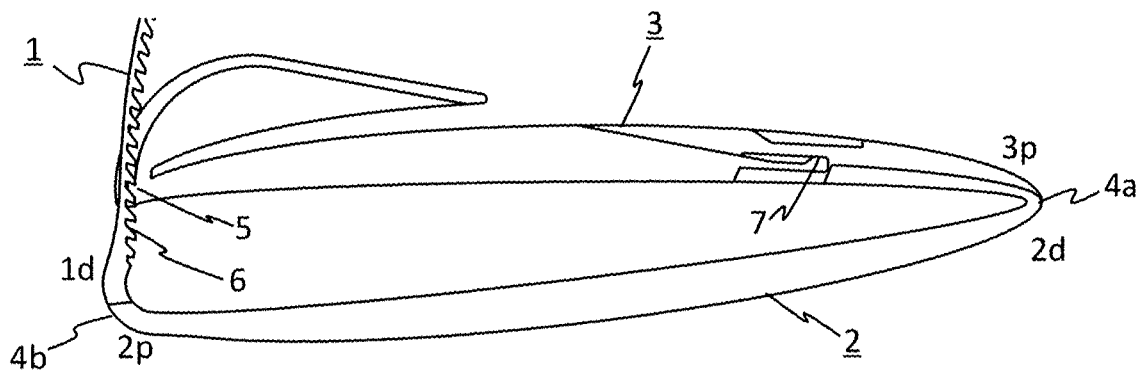
[FIG. 26]
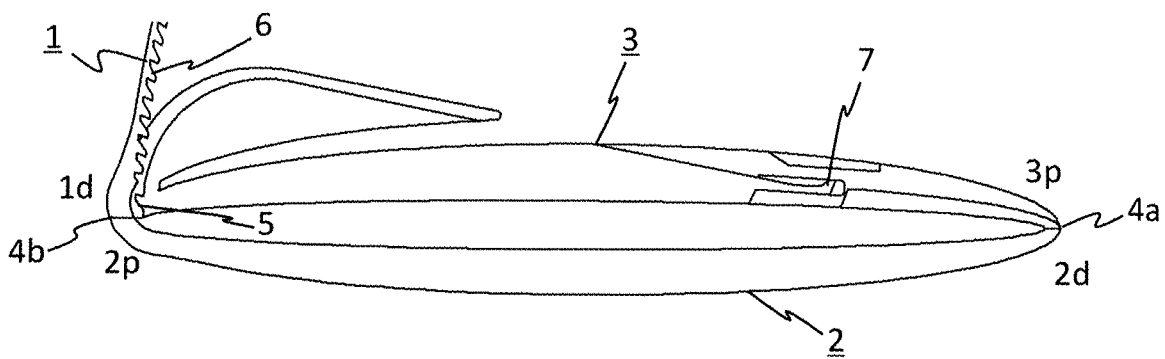

[FIG. 27]
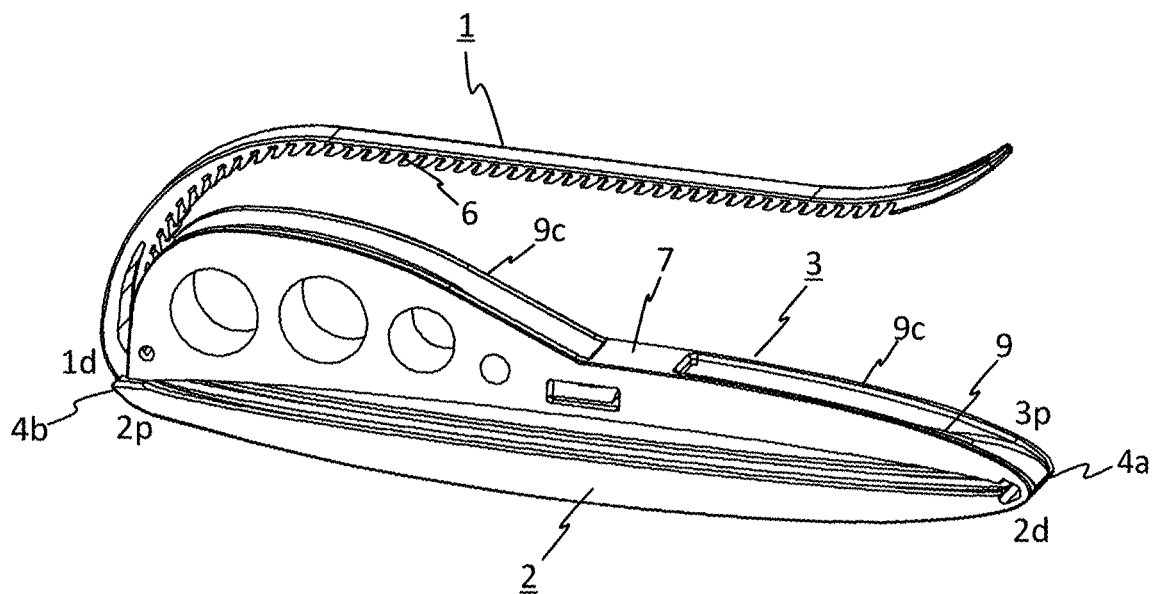
[FIG. 28]
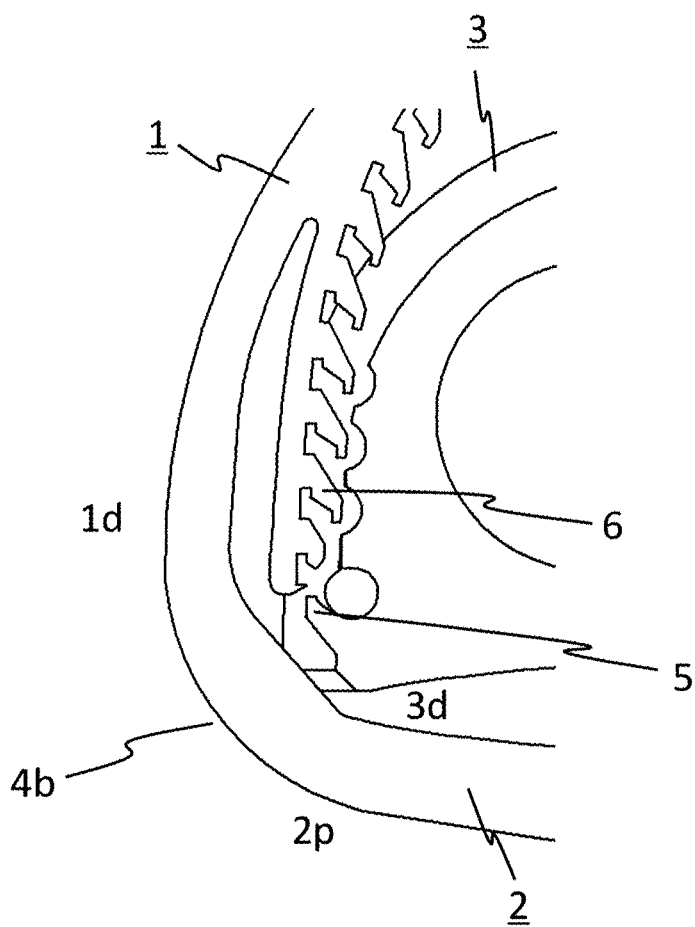

[FIG. 29]
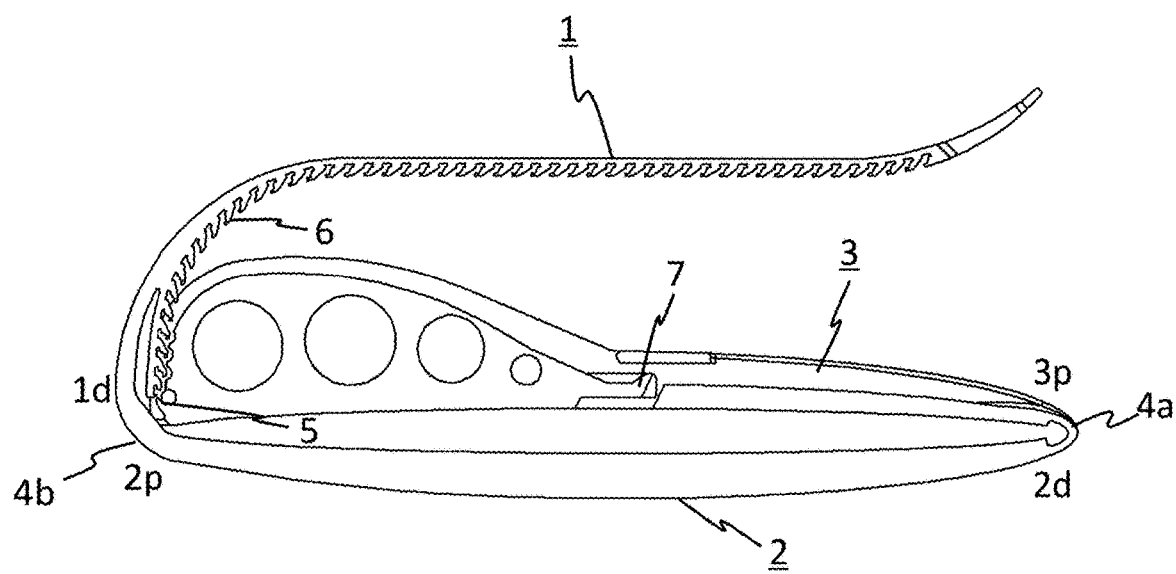

[FIG. 30]
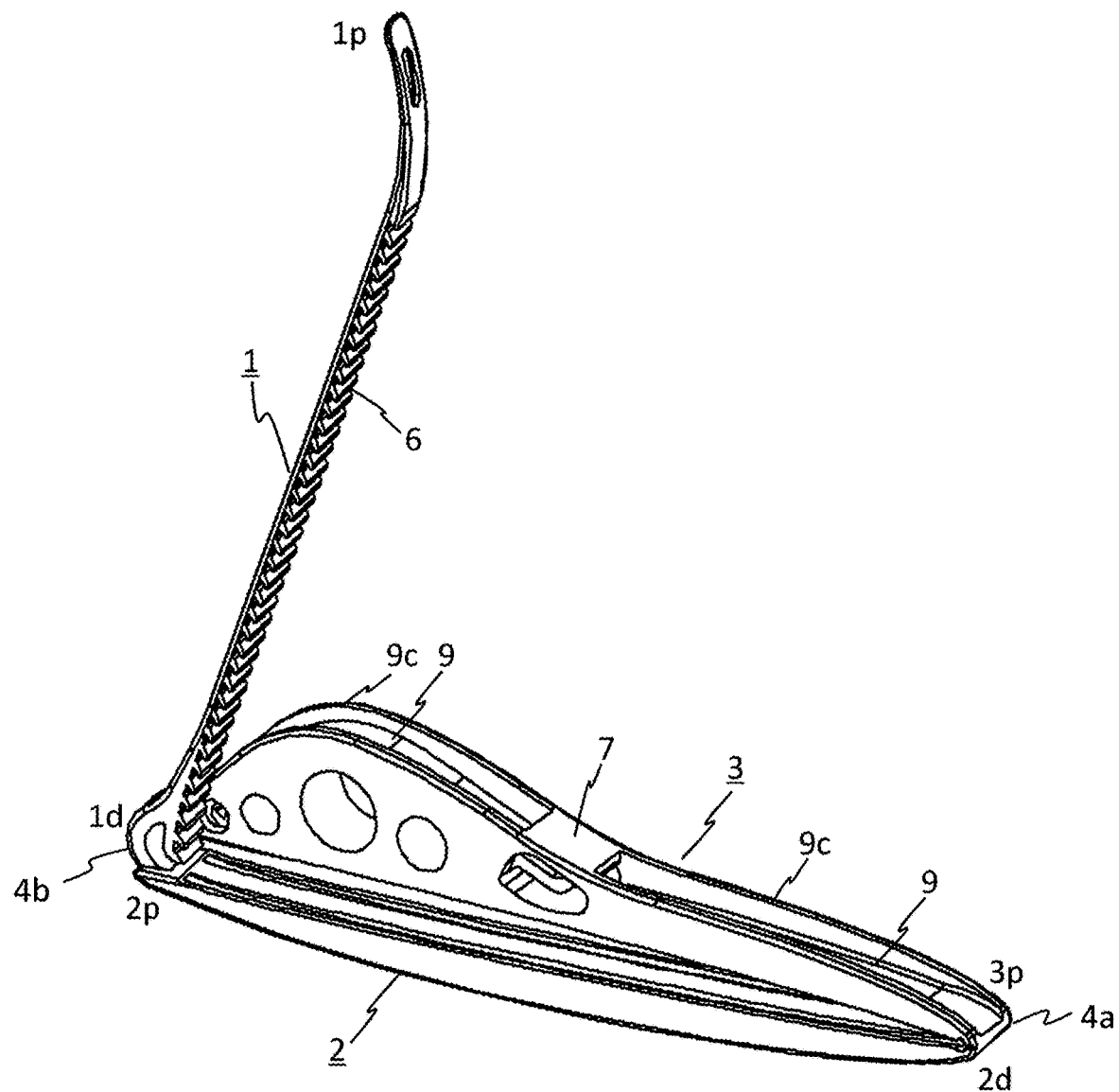

[FIG. 31]
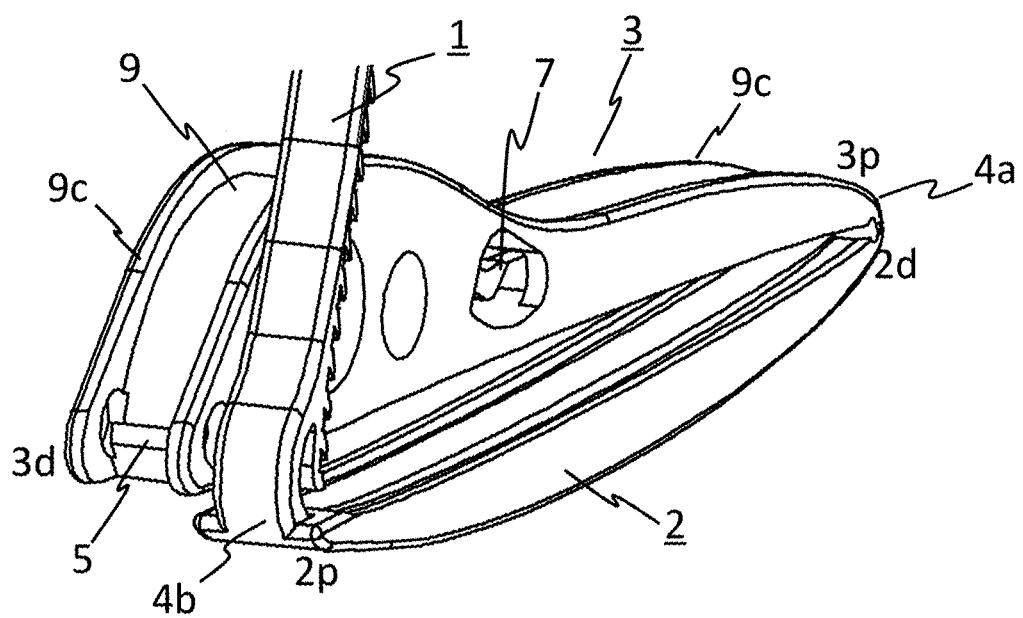

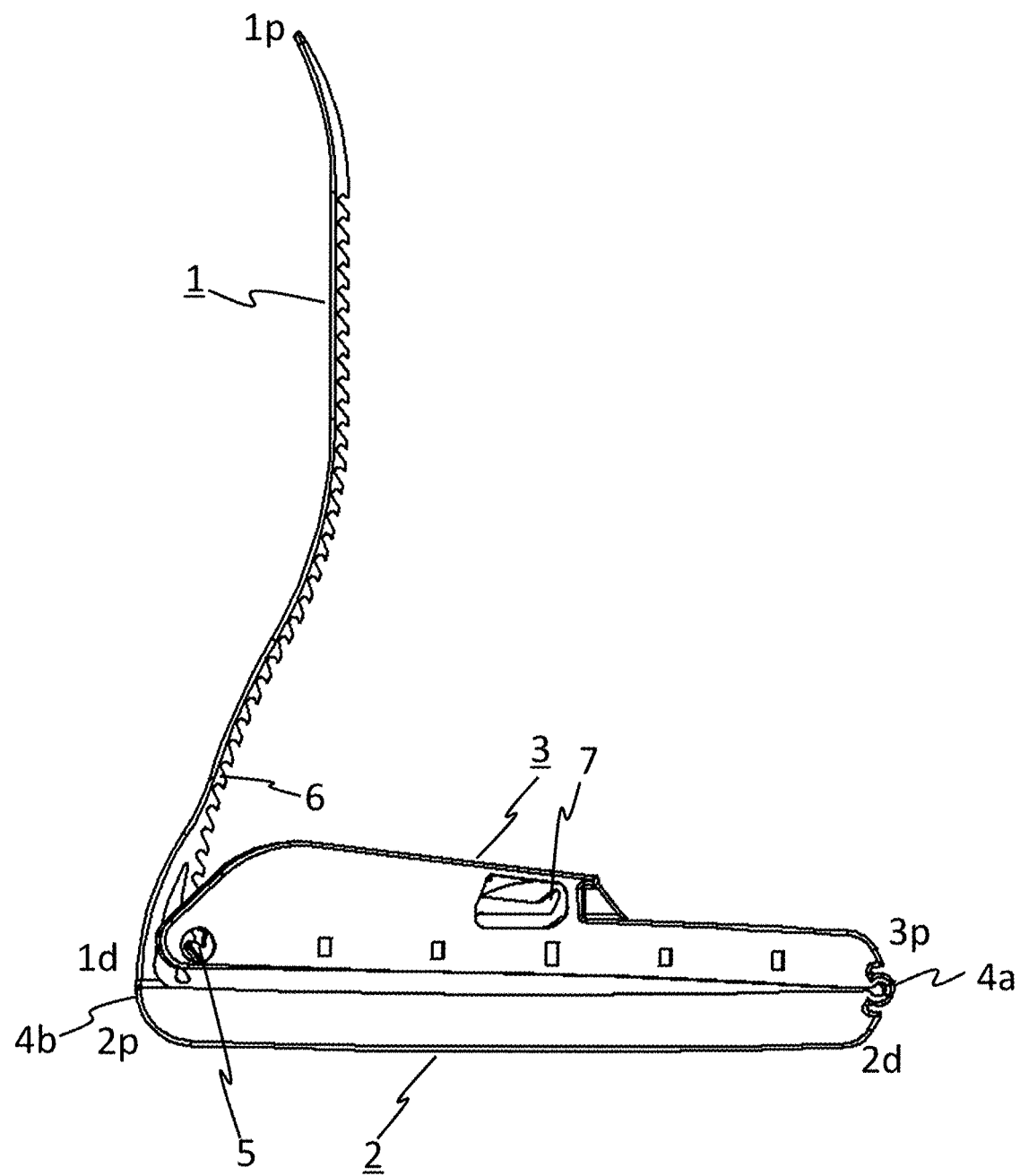
[FIG. 32]

[FIG. 33]
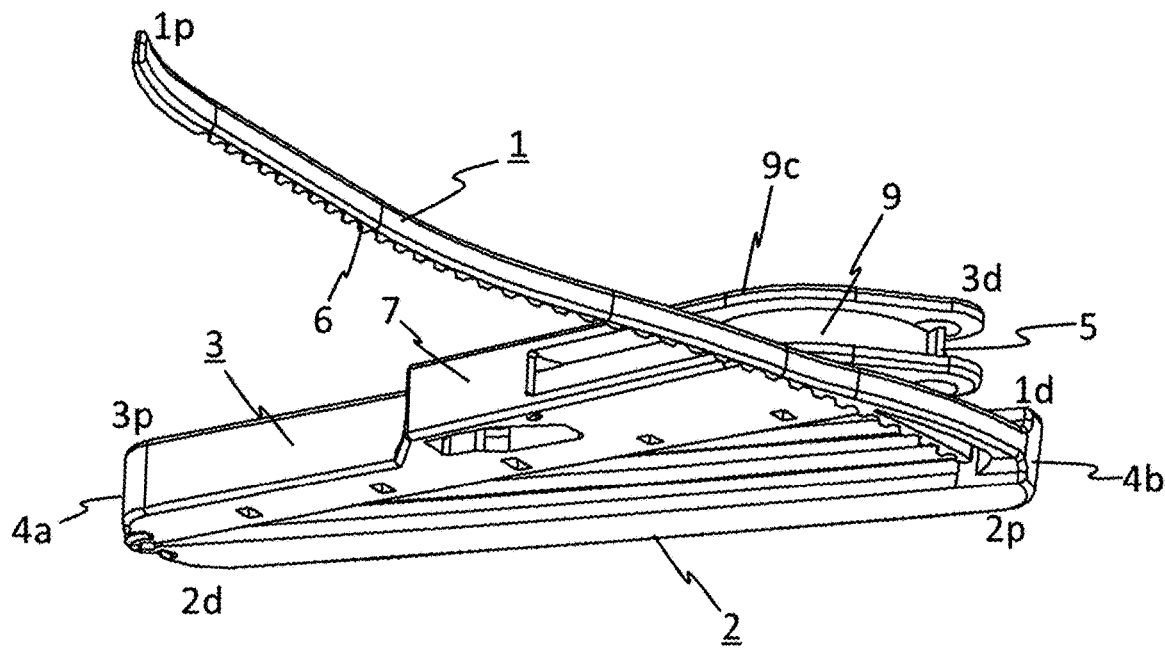
[FIG. 34]
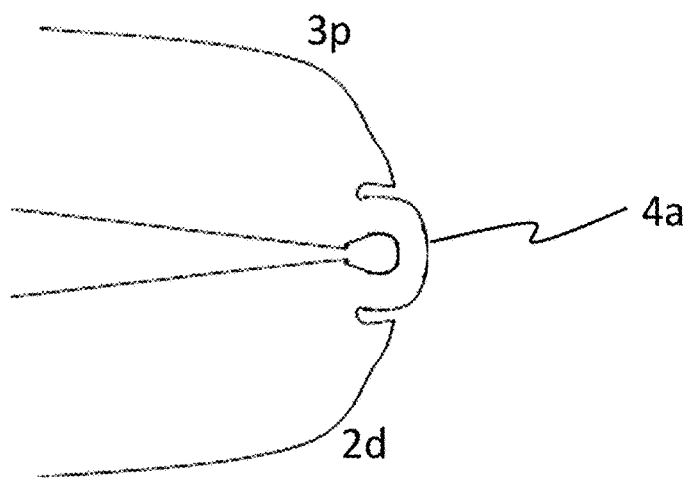

[FIG. 35]
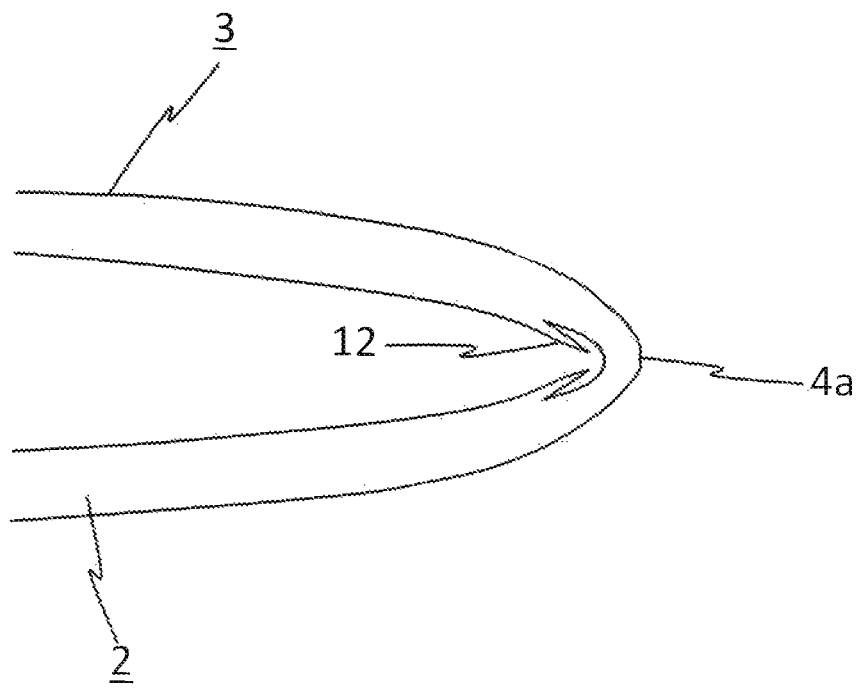
[FIG. 36]
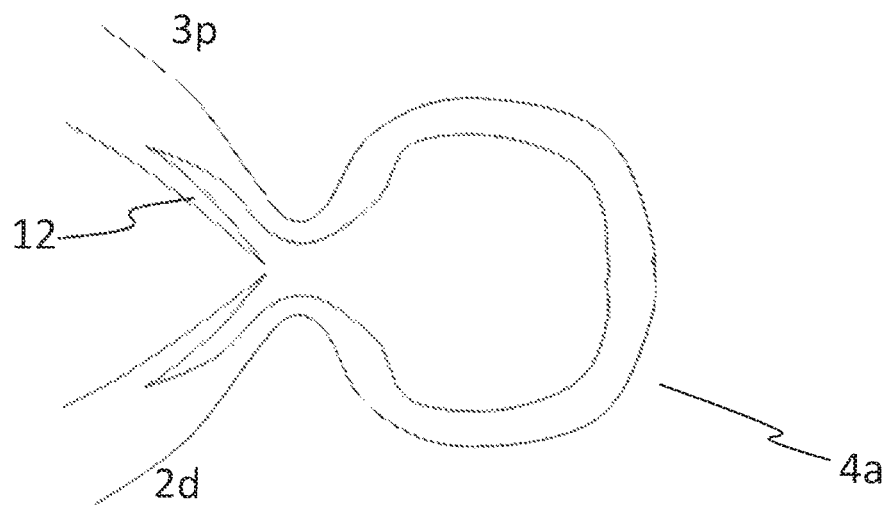

[FIG. 37]
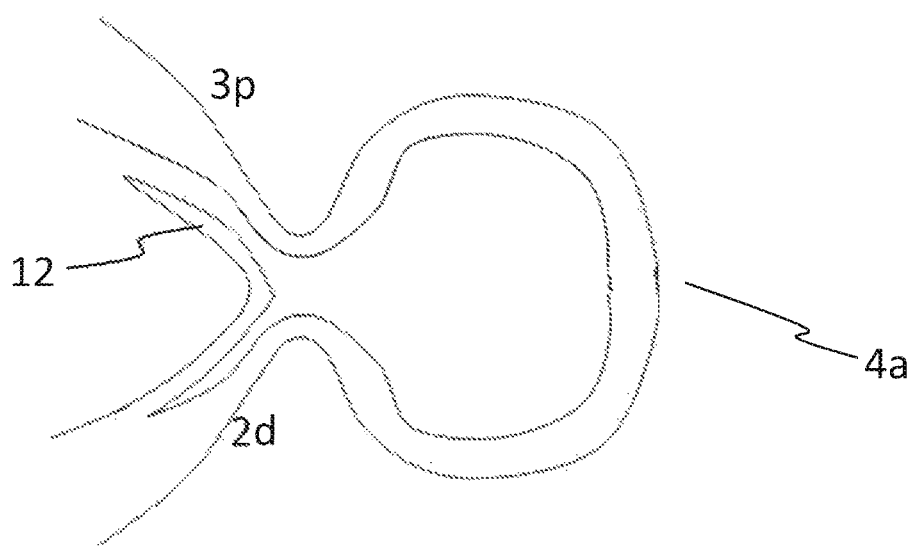
[FIG. 38]
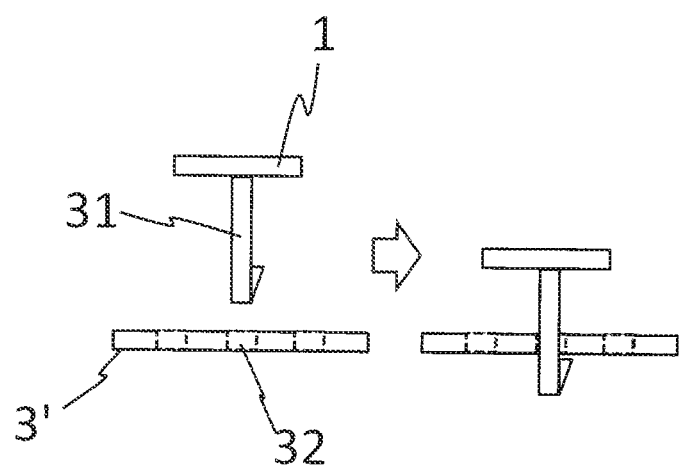

[FIG. 39]
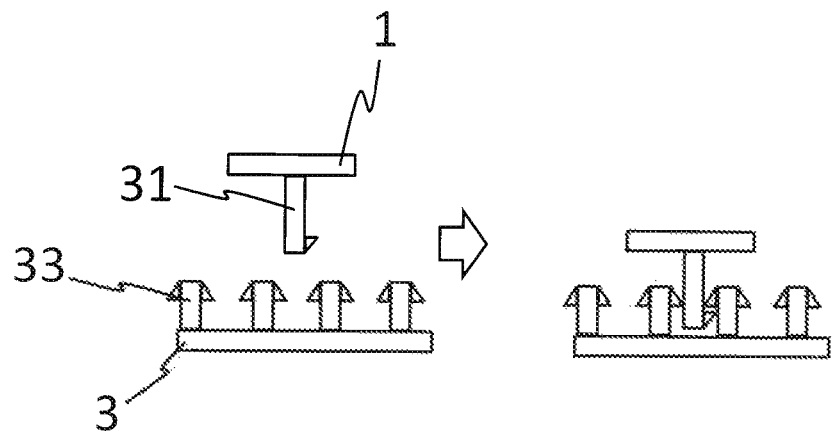
[FIG. 40]
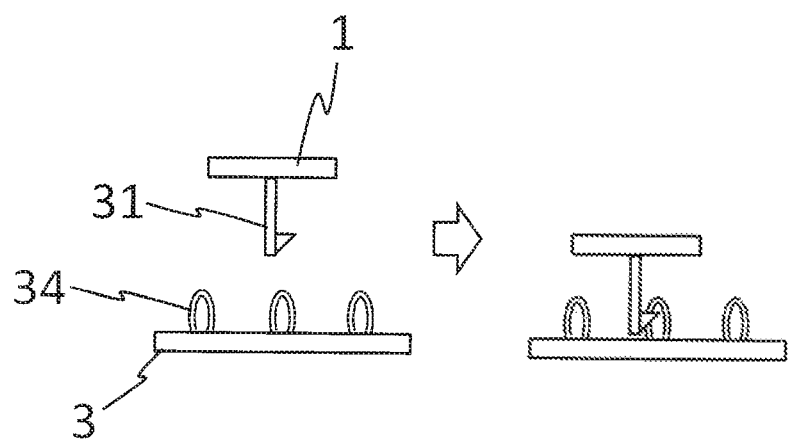
[FIG. 41]
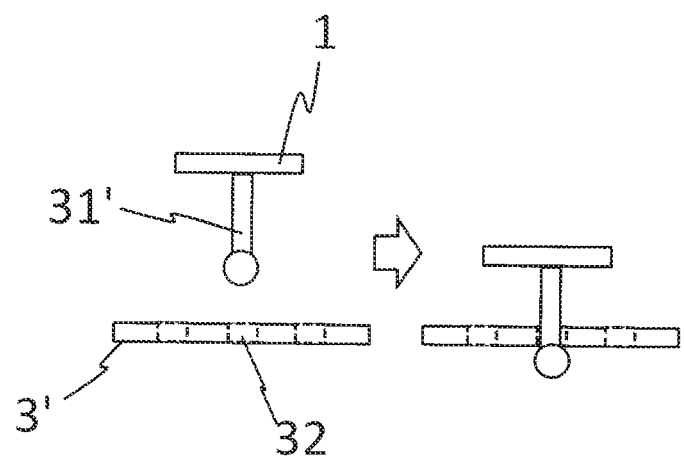

MEDICAL INSTRUMENT SUITABLE FOR LIGATURE OR SIMILAR

This application is a National Stage Entry of International Application No. PCT/JP2021/011478, filed Mar. 19, 2021, and entitled "MEDICAL INSTRUMENT SUITABLE FOR LIGATURE OR SIMILAR" which claims priority to Japanese Application No. 2020-053425, filed Mar. 24, 2020, the contents of which are incorporated by reference herein.

TECHNICAL FIELD

The present invention relates to a medical instrument. More specifically, the present invention relates to a medical instrument that can be used to prevent the occurrence of various complications in partial resection and the like of living tissue (e.g., organ, organum) such as liver, pancreas and blood vessels, and is less invasive and suitable for ligation and the like.

BACKGROUND ART

Ligation is performed, for example, to pull and fix a tissue severed due to trauma, etc., to discontinue a lumen by tying it around blood vessel, fallopian tube or the like, to bind and fix a tissue to close hernia gate, etc., or to tie up a tissue to be removed to stop the blood flow and leading to necrosis or sloughing off. Various medical instruments for performing ligation or the others have been proposed.

For example, Patent Document 1 discloses a ligation band composed of a synthetic resin molded product having flexibility as a whole, the synthetic resin molded product comprising a tourniquet body having a predetermined length, wherein a retaining mesh portions are continuously formed within the range that serves as a tightening allowance in the length direction of the tourniquet body, non-slip ribs are continuously formed at appropriate locations on the tourniquet body over the formation range of the retaining mesh portions, furthermore, at the base end of the tourniquet body, a short tunnel shape with an insertion port on one side and a feeding port on another side is formed, a buckle part is integrally formed at an appropriate place on the inside, and a buckle portion is formed with a locking hook capable of non-removably locking the retaining mesh portion of the tourniquet body rolled in from the tip.

Patent Document 2 discloses a medical device for tissue ligation, comprising an elongated flexible band having a front side portion, a rear side portion, a tip portion and a trailing end portion, wherein the band has a perforation portion and a cross rail portion defined within the band, a locking case connected to the trailing end portion of the band, wherein the locking case has a channel sized for receiving the band, and a locking member connected to the locking case, wherein the locking member is arranged in relation to the channel and is configured to connect with the perforation portion and the cross rail portion defined in the band, characterized in that the channel in the locking case includes an arching portion located on the opposite side of the locking member, the band becomes arched above the locking member when the locking member engages with the cross rail portion of the band, and it is configured to project at least partially into the arching portion.

Patent Document 3 discloses an organ stump treatment tool, for tying up the organ with a flat loop to ligate canal or cavity opened in the organ stump, comprising an elongate flexible first band portion having a distal end and a proximal end composed of a biodegradable and bioabsorbable polymer; an elongated flexible second band portion having a distal end and a proximal end composed of a biodegradable and bioabsorbable polymer; a first locking portion having a first ratchet pawl composed of a biodegradable and bioabsorbable polymer; wherein the first locking portion is formed at the distal end of the second band portion, and the distal end of the first band portion and the proximal end of the second band portion are joined; and at least one ratchet tooth that can be engaged with the first ratchet pawl is formed on the outer surface of the first band portion, the flat loop is formed by engaging the ratchet tooth and the first ratchet pawl.

Patent document 4 discloses an intestinal clamp, comprising two rigid rod-shaped bodies wherein the rod-shaped body has a flexible strip at one end; a connecting portion to which the rod-shaped body is connected; and at least one or more through holes provided in one of the strip; wherein, by inserting another of the strip distal end first, and passing it through the through hole, and an intestinal tract can be tucked in between the two rod-shaped bodies with the connecting portion as a fulcrum.

Patent Document 5 discloses a biomedical suture ligation tool, composed of a bioabsorbable material and configured to suture and ligate a living tissue by thermal deformation, wherein a main body of the suture ligation tool is made of a bioabsorbable material having a heat deformation starting temperature of 45° C. or more and 100° C. or less.

Patent document 6 discloses a surgical device, comprising a ligating clip comprising a latch member and a retaining member having a proximal end and a distal end; a resilient hinge connecting the latch member and the retaining member at the proximal end; a latch having a projection coupled to a shaft attached to the distal end of the latch member; a retainer having an aperture and a locking surface adapted to receive the latch and lock the ligating clip in a closed position at the distal end of the retaining member; a port located at the distal end of the retaining member for permitting visual inspection of an engagement of the latch and the retaining member, wherein a part of the latch member and a part of the retaining member provide a latching mechanism that is contrasting in color so that the presence of the latch member in the locked position is externally visible when the latch member is locked in place by the retaining member.

Patent document 7 discloses a surgical forceps, comprising a pair of arms and a releasable ratchet means, wherein each arm is interconnected at one end thereof to one end of the other arm by a flexible, resilient member tending to separate the arms, and each arm has an end opposite the one end; the member allows the arms to be moved toward each other until they are substantially parallel, one of the arms has an intermediate, site-engaging and clamping portion facing the other arm, and the other arm has an intermediate, site-engaging and clamping portion facing the clamping portion of said one arm; a layer of elastic material is overlain each of the opposing surfaces of the clamping portions, the material is softer than material of the clamping portions, and the ratchet means is in the opposite end of the one arm, extends toward the other arm, is engageable with the other arm near the opposite end of the other arm, and is for holding the arms in a plurality of fixed relative positions.

Patent document 8 discloses a clamp for closing an umbilical cord stump of a newborn, comprising a pair of substantially straight first and second members; spring means connected to the first ends of the members and biasing the members to a mutually inclined position; locking means on one of said members for holding said members substantially parallel and in close proximity to the force from a spring member; and an umbilical cord gripping and closing means having at least one first projection portion and corresponding first grooves in the first and second members and being defined by said members.

Patent document 9 discloses a ligating clip, comprising a first jaw comprising a body having an inner surface defining a first pinching surface and an outer surface; a second jaw comprising a body having an inner surface defining a second pinching surface and an outer surface; a hinge integrally formed with the first and second jaws, the hinge comprising an inner hinge portion and an outer hinge portion, wherein the inner hinge portion has an inner surface contiguous with the first and second pinching surfaces of the first and second jaws and an outer surface; the hinge is configured to facilitate pivoting of the first jaw relative to the second jaw between an open position and a pinched position, wherein the inner surface of the inner hinge portion is defined by a plurality of curved parts.

Patent document 10 discloses a polymer surgical clip comprising first and second curved leg members, wherein the leg members are joined at their proximal ends by resilient hinge means; each of the leg members has a vascular clip inner surface and a back-to-back outer surface; a vascular clamping inner surface of one of the leg members faces the vascular clamping inner surface of the other of the leg members; the first leg member has a flexible hook portion at the end wherein the hook portion is curved toward the second leg member; the second leg member has a lock portion at the end wherein the lock portion is complementary to the hook portion, whereby, when the first and second leg members move around the hinge means from the open position to the closed position, the hook portion flexes around the end of the second leg member to lock the clip at the closed position, the inner surface of the first leg member has a concave curvature radius between the hinge means and the hook portion; the inner surface of the second leg member has a convex curvature radius between the hinge means and the end thereof; additionally, and the outer surface of the second leg member has a concave curvature radius between the hinge means and the end thereof.

CITATION LIST

Patent Literatures

PATENT DOCUMENT 1: JP 2004-298501 A
PATENT DOCUMENT 2: JP 2015-523144 A
PATENT DOCUMENT 3: WO 2019/039586 A1
PATENT DOCUMENT 4: JP 2006-87671 A
PATENT DOCUMENT 5: JP H05-337123 A
PATENT DOCUMENT 6: JP H08-215201 A
PATENT DOCUMENT 7: JP S56-500242 A
PATENT DOCUMENT 8: U.S. Pat. No. 3,705,586 A
PATENT DOCUMENT 9: JP 2020-025856 A
PATENT DOCUMENT 10: JP H01-146536 A

SUMMARY OF THE INVENTION

Problem to be Resolved by the Invention

An object of the present invention is to provide a medical instrument suitable for ligation, etc., which can be used to prevent the occurrence of various complications in the partial resection of living tissue (organ, organum, etc.) such as liver, pancreas, and blood vessels, and which is less invasive.

Means for Resolving the Problem

Intensive studies in order to solve the above problems have resulted in completion of the present invention including the following embodiments.

[1] A medical instrument, comprising
a flexible band body having a distal end and a proximal end;
a flexible first rod-shaped body having a distal end and a proximal end; and
a flexible second rod-shaped body having a distal end and a proximal end,
wherein
the distal end of the band body and the proximal end of the first rod-shaped body are connected,
the distal end of the first rod-shaped body and the proximal end of the second rod-shaped body are connected via a connecting portion,
the band body is more flexible than the first rod-shaped body and the second rod-shaped body,
the second rod-shaped body and the band body have a locking feature capable of tightening the band body to the second rod-shaped body at a desired position, when tightened by the locking feature, the proximal end of the first rod-shaped body and the distal end of the second rod-shaped body are connected via a part of the band body, the connecting portion is inflected, and a loop having a desired size can be formed of the first rod-shaped body, the second rod-shaped body and the part of the band body,
the second rod-shaped body further has a feature for placing the rest of the band body along an outer surface of the second rod-shaped body in the direction from the distal end to the proximal end of the second rod-shaped body when had been tightened by the locking feature.

The part of the band body constituting the loop is, specifically, a part from the distal end of the band body to the portion where the distal end of the second rod-shaped body contacts. The rest of the band body not constituting the loop is, specifically, a part from the proximal end of the band body to the portion where the distal end of the second rod-shaped body contacts.

[2] The medical instrument according to [1], wherein an inner surface of the first rod-shaped body and/or an inner surface of the second rod-shaped body are/is curved concavely inward in the central region relative to the distal and proximal ends.

[3] The medical instrument according to [1], wherein an inner surface of the first rod-shaped body and/or an inner surface of the second rod-shaped body are/is curved convexly inward in the central region relative to the distal and proximal ends.

[4] The medical instrument according to any one of [1] to [3], wherein the feature for placing the rest of the band body along an outer surface of the second rod-shaped body comprises a groove having a shape corresponding to the band body and being provided on the outer surface of the second rod-shaped body.

[5] The medical instrument according to any one of [1] to [4], wherein the outer surface of the second rod-shaped body is curved convexly outward in at least near the distal end.

[6] The medical instrument according to any one of [1] to [5], wherein the band body, the first rod-shaped body and the second rod-shaped body are composed of a biodegradable and bioabsorbable polymer.

[7] The medical instrument according to any one of [1] to [6], wherein a layer of cushioning material is respectively provided on the inner surface of the first rod-shaped body and the inner surface of the second rod-shaped body.

[8] The medical instrument according to any one of [1] to [6], wherein an inner belt is provided on the inner surface of the first rod-shaped body and the inner surface of the second rod-shaped body.

[9] The medical instrument according to any one of [1] to [8], configured to ligate a living tissue.

[10] The medical instrument according to [9], configured to be adjusted so that necrosis of the living tissue is less likely to occur even when ligated.

[11] The medical instrument according to [9], configured to be adjusted to maintain blood flow in the living tissue even when ligated.

[12] The medical instrument according to any one of [9] to [11], wherein the living tissue to be ligated is an organum.

[13] The medical instrument according to any one of [9] to [11], wherein the living tissue to be ligated is pancreas.

[14] The medical instrument according to any one of [9] to [11], wherein the living tissue to be ligated is a body or tail of pancreas.

[15] The medical instrument according to any one of [9] to [11], wherein the body tissue to be ligated is a head of pancreas.

[16] The medical instrument according to any one of [13] to [15], configured to be adjusted so that pancreatic fistula does not occur even if ligated.

[17] The medical instrument according to [9], wherein the living tissue to be ligated is liver.

[18] The medical instrument according to [9], wherein the living tissue to be ligated is blood vessel.

Advantageous Effects of the Invention

The medical instrument of the present invention is suitable for ligation of living tissue, it can be used to prevent the occurrence of various complications in partial excision of living tissue (organ, organum, etc.) such as liver, pancreas and blood vessels, and is less invasive.

BRIEF DESCRIPTION OF THE DRAWINGS

FIG. 1 is an oblique view showing an example of the medical instrument of the present invention.

FIG. 2 is an oblique view showing another example of the medical instrument of the present invention.

FIG. 3 is a view showing an example of the medical instrument in a state when the first rod-shaped body and the second rod-shaped body are closed so as to be substantially parallel.

FIG. 4 is a view showing another example of the medical instrument in a state when the first rod-shaped body and the second rod-shaped body are closed so as to be substantially parallel.

FIG. 5 is a view showing another example of the medical instrument in a state when the first rod-shaped body and the second rod-shaped body are closed so as to be substantially parallel.

FIG. 6 is a view showing another example of the medical instrument in a state when the first rod-shaped body and the second rod-shaped body are closed so as to be substantially parallel.

FIG. 7 is a conceptual partial diagram showing an example of the medical instrument viewed from the distal end to the proximal end of the second rod-shaped body, immediately before the rest of the band body is, along the outer surface of the distal end 3d of the second rod-shaped body, inserted the proximal end 1p first into an area where the ratchet pawl 5 is located.

FIG. 8 is a conceptual partial diagram showing an example of the medical instrument viewed from the lateral in the state of FIG. 7.

FIG. 9 is a conceptual partial diagram showing an example of the medical instrument viewed from the distal end to the proximal end of the second rod-shaped body, when the rest of the band body has been, along the outer surface of the distal end 3d of the second rod-shaped body, inserted the proximal end 1p first to be locked in an area where the ratchet pawl 5 is located.

FIG. 10 is a conceptual partial diagram showing an example of the medical instrument viewed from the lateral in the state of FIG. 9.

FIG. 11 is a lateral view showing an example of holes formed in the second rod-shaped body.

FIG. 12 is a view of the hole in FIG. 11 viewed from the outer surface side.

FIG. 13 is an oblique view showing another example of the medical instrument of the present invention.

FIG. 14 is an oblique view showing a main part of the medical instrument shown in FIG. 13 viewed from another direction.

FIG. 15 is an oblique view showing a main part of another example of the medical instrument of the present invention.

FIG. 16 is an oblique view showing a main part of the medical instrument shown in FIG. 15 in a state of locked.

FIG. 17 is a cross-sectional view showing the main part of the locking feature of the medical instrument shown in FIG. 16.

FIG. 18 is an oblique view showing another example of the second rod-shaped body in the medical instrument of the present invention.

FIG. 19 is a cross-sectional view showing the locking feature of the second rod-shaped body shown in FIG. 18.

FIG. 20 is an oblique view showing an example of the first rod-shaped body and the band body that can be combined with the second rod-shaped body shown in FIG. 18.

FIG. 21 is a view showing an example of the medical instrument, when connecting the distal end of the first rod-shaped body shown in FIG. 20 and the proximal end of the second rod-shaped body shown in FIG. 18 with the band body that is placed in the feature for placing band body along an outer surface of the second rod-shaped body.

FIG. 22 is an partial exploded view showing an example of the medical instrument, when connecting the distal end of the first rod-shaped body shown in FIG. 20 and the proximal end of another second rod-shaped body in the medical instrument of the present invention with the band body that is placed in the feature for placing band body along an outer surface of the second rod-shaped body.

FIG. 23 is an oblique view showing another example of the medical instrument of the present invention.

FIG. 24 is an oblique view showing a main part of the medical instrument shown in FIG. 23 viewed from another direction.

FIG. 25 is a cross-sectional view showing a main part of the medical instrument of the present invention when the band body is placed and locked in the locking feature of the second rod-shaped body.

FIG. 26 is a cross-sectional view showing another state of the medical instrument shown in FIG. 23.

FIG. 27 is an oblique view showing another example of the medical instrument of the present invention.

FIG. 28 is a view showing the locking feature of the medical instrument shown in FIG. 27.

FIG. 29 is a cross-sectional view showing the medical instrument shown in FIG. 27, when the band body is placed and locked in the locking feature of the second rod-shaped body.

FIG. 30 is an oblique view showing another example of the medical instrument of the present invention.

FIG. 31 is an oblique view showing a main part of the medical instrument shown in FIG. 30 viewed from another direction.

FIG. 32 is an oblique view showing another example of the medical instrument of the present invention.

FIG. 33 is an oblique view showing a main part of the medical instrument shown in FIG. 32 viewed from another direction.

FIG. 34 is a view showing the connecting portion 4a of the medical instrument shown in FIG. 32.

FIG. 35 is a view showing another example of the connecting portion 4a.

FIG. 36 is a view showing another example of the connecting portion 4a.

FIG. 37 is a view showing another example of the connecting portion 4a.

FIG. 38 is a view showing an example of the feature for placing the band body along the outer surface of the second rod-shaped body.

FIG. 39 is a view showing an example of the feature for placing the band body along the outer surface of the second rod-shaped body.

FIG. 40 is a view showing an example of the feature for placing the band body along the outer surface of the second rod-shaped body.

FIG. 41 is a view showing an example of the feature for placing the band body along the outer surface of the second rod-shaped body.

EMBODIMENTS FOR CARRYING OUT THE INVENTION

Embodiments of the present invention will be described with reference to the drawings.

The medical instrument of the present invention comprises a band body 1, a first rod-shaped body 2, and a second rod-shaped body 3.

The band body 1 is an elongate flexible band-like member having a distal end 1d and a proximal end 1p. The band body is preferably composed of a medical material, more preferably composed of a biocompatible polymer, and even more preferably composed of a biodegradable and bioabsorbable polymer. The band body may be formed in bulk (mass), or may be formed of fiber such as nets, woven fabrics, or non-woven fabrics.

The first rod-shaped body 2 is an elongate flexible rod-shaped member having a distal end 2d and a proximal end 2p. The second rod-shaped body 3 is an elongate flexible rod-shaped member having a distal end 3d and a proximal end 3p. The first rod-shaped body and the second rod-shaped body are preferably composed of a medical material, more preferably composed of a biocompatible polymer, and even more preferably composed of a biodegradable and bioabsorbable polymer. The first rod-shaped body and the second rod-shaped body may be formed in bulk (mass), or may be formed of fibers such as nets, woven fabrics, non-woven fabrics, etc. In order to make it difficult to bend, it is preferable to be formed in bulk.

The medical instrument of the present invention can be obtained, for example, by making the shape of each part by applying a known resin shaping method to the polymer which is a medical material. Examples of the polymer can include lactic acid polymer, lactic acid-glycolic acid polymer, trimethylene carbonate polymer, dioxanone polymer, polyethylene glycol polymer, and lactone polymer.

In addition, the band body, the first rod-shaped body and the second rod-shaped body are not particularly limited in terms of their length, thickness, elastic modulus, etc. They can be set as appropriate, for example, depending on the shape or size of the living tissue to be treated.

In the medical instrument of the present invention, the distal end of the band body 1 and the proximal end of the first rod-shaped body 2 are connected via the connecting portion 4b. It is preferable that the distal end of the band body and the proximal end of the first rod-shaped body are connected so as to be concave inward. The connecting portion 4b may be, for example, a short belt-like member or a hinge member. Further, the connecting portion 4b may have a detachable connection structure so that the first rod-shaped body 2 and the band body 1 can be connected or separated each other. The connecting portion 4b is preferably composed of a medical material, more preferably composed of a biocompatible polymer, and even more preferably composed of a biodegradable and bioabsorbable polymer.

In the medical instrument of the present invention, a distal end of the first rod-shaped body 2 and a proximal end of the second rod-shaped body 3 are connected via a connecting portion 4a. The distal end of the first rod-shaped body 2 and the proximal end of the second rod-shaped body 3 are preferably connected so as to be concave inward. The connecting portion 4a may be, for example, a short belt-like member or a hinge member. Further, the connecting portion 4a may have a detachable connection structure so that the first rod-shaped body 2 and second rod-shaped body 3 can be connected or separated each other.

The connecting portion 4a may have a shape thinner than the thickness of the proximal end 3p of the second rod-shaped body 3 and the distal end 2d of the first rod-shaped body 2 as shown in FIG. 29, Landolt's annulus shape as shown in FIG. 34, or a shape in which the peninsular portion 12 is provided on the inside as shown in FIG. 35, 36 or 37. The connecting portion 4a having such a shape can make the gap between the first rod-shaped body and the second rod-shaped body more parallel or closer, the tightening pressure applied to the living tissue can be made more uniform, and can reduce the risk of pinching the living tissue between the connecting portion 4a. The installation of the peninsular portion can effectively reduce the risk of pinching of the living tissue.

The connecting portion 4a is preferably composed of a medical material, more preferably composed of a biocompatible polymer, and even more preferably composed of a biodegradable and bioabsorbable polymer.

In addition, in the state where the locking feature described later is not used, the proximal end of the band body and the distal end of the second rod-shaped body are preferably free from any binding. A rib 8 or the like is preferably provided on the proximal end side part of the band body to make rigidity higher than that of the distal end side part of the band body, so as to suppress buckling and facilitate insertion into the locking feature.

Also, the band body is more flexible than the first rod-shaped body and the second rod-shaped body. There is no particular limitation in the method for adjusting the flexibility. For example, when the band body, the first rod-shaped body and the second rod-shaped body are made of the same material, flexibility adjustment can be carried out by adjusting the thickness or diameter. By partially increasing the thickness like the rib 8, the ease of bending can be reduced. Also, as shown in FIG. 2, flexibility can be enhanced by providing a plurality of grooves (for example, grooves between ratchet teeth 6) on the outer surface of the band body in a direction orthogonal to the bending direction.

The second rod-shaped body 3 and the band body 1 have the locking feature. The locking feature can tightens the band body to the second rod-shaped body at a desired position.

The locking feature comprises a combination of a part on the band body and a part on the second rod-shaped body which is configured to be tightly bound to the part on the band body. For example, as the locking feature, mentioned can be a combination of a ratchet pawl 5 provided on the second rod-shaped body and a plurality of ratchet teeth 6 provided on the band body along the longitudinal direction, a combination of at least one depression provided on the second rod-shaped body and a plurality of protrusions provided on the band body along the longitudinal direction, a combination of at least one protrusion provided on the second rod-shaped body and a plurality of depressions provided on the band body along the longitudinal direction, and so on.

In the locking feature, a pin, a hook, etc. are mentioned as the protrusion, a hole, a loop, a constriction, a notch and the like can be mentioned as the depression. The plurality of protrusions or depressions provided on the band body may be a string of spherical or ring-shaped objects arranged in a row, a sawtooth-shaped object projecting on both sides, or a ladder shaped objects.

The protrusion in the locking feature preferably has a barb in order to prevent it from slipping out of the depression into which it is inserted. The protrusion with a barb may have an inverted L shape, a T shape, a cross shape, or the like. The plurality of depressions provided in the band body may be meshes in cloth or net as long as the protrusions can be inserted. As a combination of hook and loop, for example, hook and loop fasteners may be used.

A ratchet, which is an example of the locking feature, is one of the mechanisms used to restrict the direction of movement to one direction. Tightening is achieved by engaging ratchet teeth 6 with ratchet pawl 5. The ratchet pawl is classified into a movable type and a fixed type. When the movable ratchet pawl is engaged with the ratchet teeth, the engagement can be easily released. When the fixed ratchet pawl engages the ratchet teeth, it is difficult to release the engagement. In the figure, only one movable ratchet pawl is provided. When a fixed ratchet pawl and a movable ratchet pawl are installed side by side, the band body is firstly locked by the movable ratchet pawl, if the tightening force on the living tissue is too tight, the engagement can be released and the tightening force can be loosened. Then, when the tightening force is determined, the fixed ratchet pawl can be engaged so that the position of the band body does not change.

When tightened by the locking feature, the proximal end of the first rod-shaped body and the distal end of the second rod-shaped body are connected via a part of the band body, specifically, a portion from the distal end of the band body to a portion where the distal end of the second rod-shaped body contacts, the connecting portion 4a can be inflected, and a loop is formed by the first rod-shaped body, the second rod-shaped body and the part of the band body. The loop may be sectorial loop, or may be a polygonal loop.

The part of the band body connecting between the proximal end of the first rod-shaped body and the distal end of the second rod-shaped body can be changed in length by changing the locking position, resulting in size change of the loop. This allows the loop to have a desired size and a desired tightening force depending on the size of the object to be ligated.

The inner surface of the first rod-shaped body and the inner surface of the second rod-shaped body, each independently, may be straight between the distal end and the proximal end; may be concavely inward curved between the distal and proximal ends, or may be curved convexly inward between the distal and proximal ends. In particular, mentioned can be, as shown in FIG. 3, the inner surface of the first rod-shaped body and the inner surface of the second rod-shaped body are both curved convexly inward between the distal end and the proximal end; as shown in FIG. 4, the inner surface of the first rod-shaped body and the inner surface of the second rod-shaped body are both curved concavely inward between the distal end and the proximal end; as shown in FIG. 5, the inner surface of the first rod-shaped body 2 is concavely curved inward between the distal end and the proximal end and the inner surface of the second rod-shaped body 3 is convexly curved inward between the distal end and the proximal end; or, as shown in FIG. 6, the inner surface of the first rod-shaped body 2 is convexly curved inward between the distal end and the proximal end and the inner surface of the second rod-shaped body 3 is concavely curved inward between the distal end and the proximal end. From the viewpoint of smooth ligation of living tissue, both of the inner surface of the first rod-shaped body and the inner surface of the second rod-shaped body are, preferably, concavely curved inward between the distal and proximal ends (see FIG. 4) or convexly curved inward between the distal and proximal ends (see FIG. 3), more preferably, concavely curved inward between the distal and proximal ends.

The inner surface of the first rod-shaped body and the inner surface of the second rod-shaped body may be a rough surface, a surface with convex streaks 13 or concave streaks 11 or a grid, or a surface having a plurality of convex or concave points, in order to increase frictional force with living tissue and prevent slippage during ligation.

By providing convex streaks parallel to the longitudinal direction near longitudinal edges of the inner surface of the first rod-shaped body and the inner surface of the second rod-shaped body, it is possible to enhance effects of preventing the leakage of digestive juice and arresting hemorrhage.

Further, a layer of cushioning material may be provided on the inner surface of the first rod-shaped body and the inner surface of the second rod-shaped body in order to make the living tissue less likely to be damaged when tightened. Examples of the cushioning material can include soft elastic bodice such as rubber, foamed elastic bodies such as sponge, non-woven such as felt and woven fabrics. The cushioning material is preferably composed of a medical material, more preferably composed of a biocompatible polymer, and even more preferably composed of a biodegradable and bioabsorbable polymer.

When the living tissue is ligated, a gap is generated between the first rod-shaped body and the second rod-shaped body in a state of substantially parallel and the living tissue can escape into the gap. In order to prevent the living tissue from escaping into the gap, a band-shaped member (inner belt 10) can be installed so as to surround the part of the living tissue to be ligated or can be installed near the inner side of the connecting portion 4a or 4b as shown in FIG. 2. The inner belt is preferably composed of a medical material, more preferably composed of a biocompatible polymer, and even more preferably composed of a biodegradable and bioabsorbable polymer. The inner belt may be formed in bulk, or may be formed of fibers such as non-woven fabric, woven fabric, and net. In addition, when ligating, the unrestrained terminal part of the inner belt 10 as shown in FIG. 2 can be fixed by sandwiching it between the second rod-shaped body and the living tissue, by attaching to an attachment structure corresponding to the inner belt provided on the second rod-shaped body or the like.

The second rod-shaped body 3 has a feature for placing the rest of the band body along an outer surface of the second rod-shaped body in the direction from the distal end to the proximal end of the second rod-shaped body, when had been tightened by the locking feature. The rest of the band body not constituting the loop is, specifically, a part from the proximal end of the band body to the portion where the distal end of the second rod-shaped body contacts.

As the feature for placing the rest of the band body along an outer surface of the second rod-shaped body, mentioned can be, for example, a belt loop 7 through which a band body placed on the outer surface of the second rod-shaped body can be inserted; a groove 9 having a shape corresponding to the band body placed on the outer surface of the second rod-shaped body; holes, loops, hooks, barbed pins, etc. provided on the outer surface of the second rod-shaped body corresponding to barbed pins, hooks, loops, holes, etc. provided on the inner surface of the band body and the like. A ratchet pawl may be provided on the belt loop 7 for fixing the band body. Also, in order to fold the band body 1 at the distal end of the second rod-shaped body 3 and smoothly follow the outer surface of the second rod-shaped body, the outer surface of the second rod-shaped body preferably has a structure that is convexly curved outward at least near the distal end thereof. This structure preferably has a shape that the band body 1 closely contacts the outer surface of the second rod-shaped body when the band body 1 is fastened to the locking feature. When the band body 1 is locked in close contact as described above, the distance from the distal end 1d of the band body 1 to the part of the band body 1 in contact with the distal end of the second rod-shaped body does not increase, and a stable clamping force to the living tissue can be obtained and it is difficult to loosen. Also, this structure can guide the direction of the ratchet teeth on the band body 1 with respect to the ratchet pawl on the second rod-shaped body in such a direction that the engagement between them can be ensured. With this structure, it is possible to prevent the band body 1 from being oriented in an inappropriate direction for engagement and from applying a large load to the ratchet pawl, thereby reducing a risk of breakage to the ratchet pawl. For example, FIGS. 7 to 10 show stages from insertion of the band body 1 into the ratchet pawl 5 to lock of the band body. The distal end 3d of the second rod-shaped body has a groove 9 having a size corresponding to the width of the band body 1 by ridges 9c provided on both sides thereof, as shown in FIG. 7. The groove 9 guides the band in the proper direction and prevents lateral slippage. Also, the vicinity of the distal end 3d of the second rod-shaped body has an outwardly convex curved outer surface, as shown in FIG. 8. When the band body 1 is passed through the movable ratchet pawl 5 its proximal end 1p side first, the band body 1 fits in the groove 9 along the outer surface of the second rod-shaped body (FIGS. 9 and 10).

A pile-and-hook mechanism or a hole-and-hook mechanism can be used as the feature for placing the band body along the outer surface of the second rod-shaped body. The pile and hook mechanism is composed of a pair of pile (thin loop) and hook, and the projection of the hook is entangled with the pile for fastening. Untangling thereof allows the hook and the pile to be pulled apart.

In the present invention, a pair of hooks and piles can be respectively provided on the inner surface of the band body and the outer surface of the second rod-like body, the band body can be fixed along the outer surface of the second rod-shaped body by pile and hook mechanism. The hole and hook mechanism is composed of a pair of hole and hook, and the hook is fitted into the hole for fastening. The projection of the hook catches on the edge of the hole and makes it difficult for the hook to come off. Releasing the catching allows the hook and the hole to be pulled apart.

In the present invention, a hook can be provided on the inner surface of the band body, and a hole can be provided on the outer surface of the second rod-shaped body, thereby the band body can be fixed along the outer surface of the second rod-shaped body by the hole and hook mechanism. Note that the holes do not have to be through holes. Specific examples thereof can include a pair of orifice 32 and hook 31 (FIG. 38), a pair of opposing hook 33 and hook 31 (FIG. 39), a pair of pile 34 and hook 31 (FIG. 40), etc. The hook 31 may be a pin 31' having a barbed shape on its head (FIG. 41).

A place where the pile-and-hook mechanism (hook-and-loop fastener) or the hole-and-hook mechanism is installed on the second rod-shaped body is not particularly limited as long as is a place that is suitable for placing along the outer surface of the second rod-shaped body. As examples of the place, in FIG. 21, mentioned can be the outer surface of the second rod-shaped body sandwiched between the ridges 9c; the outer surface of the second rod-shaped body at that position instead of the belt loop 7; the outer surface of the second rod-shaped body between the ratchet pawl 5 and the belt loop 7 and the like. As the installation location of the pile and hook mechanism (hook and loop fastener) and the hole and hook mechanism on the band body, mentioned can be the inner surface of the band body beside the row of ratchet teeth, the inner surface of the band body at the position where the ratchet teeth are partially pulled out, and the like.

FIGS. 13 and 14 are views showing another example of the medical instrument of the present invention. In the medical instrument as shown in FIGS. 13 and 14, concave streaks are provided in parallel with the longitudinal direction on the inner surfaces of the first rod-shaped body and the second rod-shaped body, the inner surfaces of the first rod-shaped body and the second rod-shaped body can be surfaces in contact with living tissue. The living tissue bites into the concave streaks to ensure the ligation and provide an anti-slip effect.

The medical instrument of the present invention as shown in FIGS. 15 to 17 has a ratchet pawl 5 facing inward on the bulging part on the distal end 3d side of the second rod-shaped body 3. The second rod-shaped body 3 is slightly longer than the first rod-shaped body 2.

FIG. 18 or 19 is a view showing a second rod-shaped body 3 that constitutes a medical instrument that is an example of the present invention. FIG. 20 shows a first rod-shaped body 2 and a band body 1 that can be combined with the second rod-shaped body 3 shown in FIG. 18 or FIG. 19. A hook 4a' is provided at the proximal end 3p of the second rod-shaped body 3, and a shaft 4a" that can be engaged with the hook 4a' is provided at the distal end 2d of the first rod-shaped body 2. The connecting portion 4a is formed by engaging the hook 4a' and the shaft 4a". In this embodiment, the band body 1 is provided with ratchet teeth 6 facing inward, the second rod-shaped body 3 has a bulge portion and a belt loop 7 in the distal end 3d side of the second rod-shaped body 3, a ratchet pawls facing outward are respectively provided inside the belt loop 7 and on the bulge portion. As shown in FIG. 21 or 22, the ratchet teeth 6 can be engaged with the ratchet pawl 5 on the bulge portion in the distal end 3d side of the second rod-shaped body 3. Furthermore, the band body 1 can be passed through the belt loop 7 and the ratchet teeth 6 can be engaged with the ratchet pawl inside the belt loop 7. In addition, in FIG. 22, the distal side portion and ratchet teeth of the band body (indicated as "1" and "6" in FIG. 22, respectively) and the proximal side portion and ratchet teeth of the band body (indicated as "(1)" and "(6)" respectively in FIG. 22) are originally connected, but the drawing between them is omitted.

The medical instrument as shown in FIGS. 23-26 has a ratchet pawl 5 at the distal end 3d of the second rod-shaped body 3. There are no ratchet teeth 6 near the distal end 1d. Even if the band body is pulled to the point where there are no ratchet teeth, relaxing the force that pulls the band body results in the ratchet pawl 5 engaged back to the ratchet teeth closest to the distal end 1d. This allows the tightening limit to be set. Also, there is a clearance gap between the bulge portion and a main portion at the distal end 3d of the second rod-shaped body. The ratchet pawl can be detached from the ratchet teeth by pushing the bulge portion to narrow the clearance gap and to bring closer to the main portion of the second rod-shaped body.

The medical instrument as shown in FIGS. 27 to 29 has a clearance gap between the ratchet teeth provided near the distal end 1d of the band body and a main portion of the band body. Even if the band body loosens unexpectedly, it is hard to disengage. In the medical instrument as shown in FIG. 29, the connecting portion 4a is formed thinner than the proximal end 3p of the second rod-shaped body 3 and the distal end 2d of the first rod-shaped body 2.

In the medical instrument as shown in FIGS. 30 to 31, the distal end 3d of the second rod-shaped body 3 and the proximal end 2p of the first rod-shaped body 2 are out of alignment so that the band body 1 does not drift into the groove 9, which can prevent the ratchet pawl and the ratchet tooth from involuntarily engaging. Since the connecting portion 4a is flexible, when the distal end 3d of the second rod-shaped body 3 and the proximal end 2p of the first rod-shaped body 2 are arranged so that the band body 1 is deep into the groove 9, the ratchet pawl and the ratchet teeth can be engaged.

The medical instrument as shown in FIGS. 32 to 33 is the same machinery as the medical instrument as shown in FIGS. 30 to 31 except that the shape of the first rod-shaped body and the second rod-shaped body are changed and the connecting portion 4a is composed of a flexible integrally molded member having a Landolt ring-shaped cross section as shown in FIG. 34. In the medical instrument shown in FIG. 32, the connecting portion 4a forming the Landolt ring is thinner than the proximal end 3p of the second rod-shaped body 3 and the distal end 2d of the first rod-shaped body 2, and the proximal end 3p of the second rod-shaped body 3 and the distal end 2d of the first rod-shaped body 2 are respectively connected to regions of discontinuity in the Landolt ring.

The medical instrument of the present invention can be used, for example, for ligating living tissue. Such living tissue is not particularly limited as long as ligation treatment is effective, and it can be used for organum, and particularly preferably for organ. Examples of such organum can include organum having tubular structure such as blood vessel, lymphatic vessel, thoracic duct, bile duct, fallopian tube, vagina, ureter, urethra, vas deferens, trachea, and bronchi. Examples of organ can include pancreas, liver, gallbladder, spleen, lien, kidney, bladder, uterus, ovary, testicle, lung, heart, thyroid, esophagus, stomach, duodenum, small intestine, large intestine, and lymph node.

The medical instrument of the present invention can be used preferably for pancreas ligation, more preferably for ligation of the body or tail of the pancreas in pancreatectomy.

The medical instrument of the present invention can be used preferably for liver ligation, more preferably for ligation of liver parenchyma at the time of bleeding from the liver, and it can be used to reduce bleeding from the liver during hepatectomy.

The medical instrument of the present invention can be used preferably for splenic ligation, more preferably for ligation of splenic parenchyma at the time of bleeding from the spleen, and it can be used to reduce bleeding from the spleen during splenectomy.

The medical instrument of the present invention can be used preferably for kidney ligation, more preferably for ligation of renal parenchyma at the time of bleeding from the kidney, and it can be used to reduce bleeding from the kidney during nephrectomy.

Living tissue, especially organs, are easily deformed and fragile. Conventional ligating instruments used to ligate a stump of the living tissue, in order to minimize tissue damage due to ligation such as tissue necrosis due to inhibition of blood flow in the tissue, usually have a shape that approximates the outline of a cut surface of an organ so as to apply pressure as evenly as possible to the cut surface of the organ. For example, in the case of pancreas stump treatment, a substantially circular ligating instrument has been conventionally used.

By the way, if there is a luminal structure in living tissue, cutting of the living tissue results in exposure of an opening of the luminal structure on the cut surface. And if a liquid, such as digestive juice, that may damage the surrounding tissues, is contained in the luminal structure, preventing the leakage is also a problem during ligation of living tissue. For example, it is pancreatic fistula.

However, in a conventional substantially circular ligating instrument, loose ligature is used to avoid excessive pressure on living tissue, resulting that it is not possible to effectively block the opening of the luminal structure on the cut surface of the living tissue. On the other hand, if the occlusion of the luminal structure is emphasized, excessive pressure is applied to the living tissue, so the problems of blood flow inhibition in living tissue and resulting tissue necrosis become noticeable. That is, there is a trade-off relationship between the demand for reduction of tissue injury due to ligation and the demand for suppression of liquid leakage from the luminal structure opening in the cut surface of the living tissue.

As described above, the medical instrument of the present invention comprises the first rod-shaped body and the second rod-shaped body having a specific shape and specific flexibility, and the locking feature configured to allow adjustment to maintain proper distance between the proximal end of the first rod-shaped body and the distal end of the second rod-shaped body at the time of ligation, so it can be adjusted to minimize blood flow inhibition in the living tissue due to pressurization and necrosis caused thereby, although it is not a structure that applies pressure evenly from the surroundings of living tissue. According to the medical instrument of the present invention, even if there is a luminal structure in the living tissue, the opening can be effectively closed.

Therefore, the medical instrument of the present invention can both reduce tissue damage due to ligation and suppress liquid leakage from the lumen structure opening in the cut surface of living tissue. In addition, by adjusting the force of ligating the pancreas, the medical instrument of the present invention can be secured to the pancreas while preserving the opening of the luminal structure and carrying out saturation of gastrointestinal tracts or tissues as described later in pancreatoenterostomy.

Also, as shown in FIGS. 11 and 12, the second rod-shaped body 3 and the first rod-shaped body 2 of the medical instrument of the present invention may have holes (sometimes called eyelet holes) 25 wherein openings of the holes are arranged in at least one line along the length direction. A thread can be passed through the hole 25 to sew the gastrointestinal tract, tissue, etc. to a stump of digestive organ.

The medical instrument of the present invention having holes 25 is fixed to the pancreas after pancreaticoduodenectomy and the suture needle is simply passed through the holes 25, resulting that the suture thread can be attached to the pancreas without piercing the pancreatic parenchyma with a suture needle. The pancreas with the suture thread can then be sutured to other organs such as the intestine or stomach in pancreatoenterostomy or the like.

The medical instrument of the present invention is not limited to the embodiments shown in the drawings, and the technical scope of the present invention include changing the shape, size, color, or material of each of the above members, or addition of well-known or commonly used parts other than the above-mentioned members.

CODE EXPLANATION

1: Band body
2: First rod-shaped body
3: Second rod-shaped body
4a: Connecting portion between the first rod-shaped body and the second rod-shaped body
4b: Connecting portion between the band body and the first rod-shaped body
5: Ratchet pawl
6: Ratchet teeth
7: Belt loop
8: Rib
9: Groove
9c: Ridge
10: Inner belt
11: Slip resistance (concave streaks)
12: Peninsular portion
13: Convex streaks
25: Hole
1p: Proximal end of the band body
1d: Distal end of the band body
2p: Proximal end of the first rod-shaped body
2d: Distal end of the first rod-shaped body
3p: Proximal end of the second rod-shaped body
3d: Distal end of the second rod-shaped body
4a': Hook
4a''': Shaft
31: Hook
31': Pin
32: Hole
33: Opposing hook
34: Pile
3': Wall outside of the second rod-shaped body

The invention claimed is:

1. A medical instrument, comprising
a flexible band body having a distal end and a proximal end;
a flexible first rod-shaped body having a distal end and a proximal end; and
a flexible second rod-shaped body having a distal end and a proximal end,
wherein
the distal end of the band body and the proximal end of the first rod-shaped body are connected,
the distal end of the first rod-shaped body and the proximal end of the second rod-shaped body are connected via a connecting portion,
the band body is more flexible than the first rod-shaped body and the second rod-shaped body,
the second rod-shaped body and the band body have a locking feature capable of tightening the band body to the second rod-shaped body at a desired position,
when tightened by the locking feature, the proximal end of the first rod-shaped body and the distal end of the second rod-shaped body are connected via a part of the band body, the connecting portion is inflected, and a loop having a desired size can be formed by the first rod-shaped body, the second rod-shaped body and the part of the band body,
the second rod-shaped body further has a feature for placing the rest of the band body along an outer surface of the second rod-shaped body in a direction from the distal end to the proximal end of the second rod-shaped body when tightened by the locking feature;
wherein the feature for placing the rest of the band body along the outer surface of the second rod-shaped body comprises a groove having a shape corresponding to the band body and being provided on the outer surface of the second rod-shaped body.

2. The medical instrument according to claim 1, wherein an inner surface of the first rod-shaped body and/or the second rod-shaped body are/is curved concavely inward in a central region relative to the distal and proximal ends of the first rod-shaped body and/or the second rod-shaped body.

3. The medical instrument according to claim 1, wherein an inner surface of the first rod-shaped body and/or the second rod-shaped body are/is curved convexly inward in a central region relative to the distal and proximal ends of the first rod-shaped body and/or the second rod-shaped body.

4. The medical instrument according to claim 1, wherein the outer surface of the second rod-shaped body is curved convexly outward in at least near the distal end of the second rod-shaped body.

5. The medical instrument according to claim 1, wherein the band body, the first rod-shaped body and the second rod-shaped body are composed of a biodegradable and bioabsorbable polymer.

6. The medical instrument according to claim 1, wherein a layer of cushioning material is respectively provided on an inner surface of the first rod-shaped body and an inner surface of the second rod-shaped body.

7. The medical instrument according to claim 1, wherein an inner belt is provided on an inner surface of the first rod-shaped body and an inner surface of the second rod-shaped body.

8. The medical instrument according to claim 1, configured to ligate a living tissue.

9. The medical instrument according to claim 8, configured to be adjusted so that necrosis of the living tissue is less likely to occur even when ligated.

10. The medical instrument according to claim 8, configured to be adjusted to maintain blood flow in the living tissue even when ligated.

11. The medical instrument according to claim 8, wherein the living tissue to be ligated is an organum.

12. The medical instrument according to claim 8, wherein the living tissue to be ligated is a pancreas.

13. The medical instrument according to claim 12, configured to be adjusted so that a pancreatic fistula does not occur even if ligated.

14. The medical instrument according to claim 8, wherein the living tissue to be ligated is a body or tail of a pancreas.

15. The medical instrument according to claim 8, wherein the body tissue to be ligated is a head of a pancreas.

16. The medical instrument according to claim 8, wherein the living tissue to be ligated is a liver.

17. The medical instrument according to claim 8, wherein the living tissue to be ligated is a blood vessel.

* * * * *